US012788444B2

(12) United States Patent
Ahmadi et al.

(10) Patent No.: US 12,788,444 B2
(45) Date of Patent: Nov. 10, 2026

(54) ORTHOPAEDIC ASSEMBLIES, BONE FASTENERS, HEADS AND PACKAGES WITH SUCH ASSEMBLIES, SCREWS AND/OR HEAD, AS WELL AS METHODS FOR ASSEMBLING AN ORTHOPAEDIC ASSEMBLY

(71) Applicant: AM Solutions Holding B.V., The Hague (NL)

(72) Inventors: Seyed Mohammad Ahmadi, The Hague (NL); Banafsheh Sajadi, The Hague (NL)

(73) Assignee: AM Solutions Holding B.V., The Hague (NL)

( * ) Notice: Subject to any disclaimer, the term of this patent is extended or adjusted under 35 U.S.C. 154(b) by 186 days.

(21) Appl. No.: 18/278,973

(22) PCT Filed: Mar. 10, 2022

(86) PCT No.: PCT/NL2022/050133
§ 371 (c)(1),
(2) Date: Aug. 25, 2023

(87) PCT Pub. No.: WO2022/191707
PCT Pub. Date: Sep. 15, 2022

(65) Prior Publication Data

US 2024/0138883 A1 May 2, 2024

(30) Foreign Application Priority Data

Mar. 12, 2021 (NL) ..................................... 2027748

(51) Int. Cl.
*A61B 17/70* (2006.01)

(52) U.S. Cl.
CPC ...... *A61B 17/7037* (2013.01); *A61B 17/7032* (2013.01); *A61B 17/7038* (2013.01)

(58) Field of Classification Search
CPC .... A61B 17/7032–17/7038; A61B 2017/8655; A61B 17/863; A61B 17/7275; A61B 17/7258
See application file for complete search history.

(56) References Cited

U.S. PATENT DOCUMENTS 6,127,597 A 10/2000 Beyar et al.
8,535,380 B2 9/2013 Greenhalgh et al.
(Continued)

FOREIGN PATENT DOCUMENTS

DE 10 2015 110 202 B3 6/2016
EP 3 092 976 A1 11/2016
(Continued)

OTHER PUBLICATIONS

International Search Report and Written Opinion for International Application No. PCT/NL2022/050133, mailed Apr. 25, 2022.
(Continued)

*Primary Examiner* — Julianna N Harvey
(74) *Attorney, Agent, or Firm* — Wolf, Greenfield & Sacks, P.C.

(57) ABSTRACT

An orthopaedic assembly comprises a bone fastener and a head. The bone fastener comprises a shaft with a proximal end and a distal end. The proximal end forms a tip of the bone fastener. A head post is located at the distal end, for mounting a separate head on the bone fastener. The head and the head post are each provided with a respective part of a mount for mounting the head on the head post. The mount comprises an opening in a first lockable part in which a second lockable part of the mount can be admitted. The head is mountable on the head post by moving the head towards the head post and thereby sliding the first lockable part over the second lockable part in a sliding direction, to admit the second lockable part in the opening. The head is lockable in position on the head once the second lockable part is
(Continued)

admitted to a predetermined depth into the opening by turning the first lockable part around an axis extending in the sliding direction.

19 Claims, 14 Drawing Sheets

(56) References Cited

U.S. PATENT DOCUMENTS

| | | | | |
|---|---|---|---|---|
| 8,974,507 | B2 * | 3/2015 | Eisermann | A61B 17/7034 606/305 |
| 8,986,349 | B1 | 3/2015 | German et al. | |
| 10,238,443 | B2 | 3/2019 | Seifert et al. | |
| 2003/0004575 | A1 | 1/2003 | Erickson | |
| 2005/0278036 | A1 | 12/2005 | Leonard et al. | |
| 2006/0111715 | A1 | 5/2006 | Jackson | |
| 2006/0212118 | A1 | 9/2006 | Abernathie | |
| 2006/0287725 | A1 | 12/2006 | Miller | |
| 2007/0173826 | A1 | 7/2007 | Canaveral et al. | |
| 2008/0195159 | A1 | 8/2008 | Kloss et al. | |
| 2009/0024217 | A1 | 1/2009 | Levy et al. | |
| 2009/0292361 | A1 | 11/2009 | Lopez | |
| 2010/0211114 | A1 | 8/2010 | Jackson | |
| 2010/0292796 | A1 | 11/2010 | Greenhalgh et al. | |
| 2011/0106174 | A1 * | 5/2011 | Rezach | A61B 17/7038 606/305 |
| 2011/0112578 | A1 * | 5/2011 | Keiser | A61B 17/7032 606/264 |
| 2012/0010668 | A1 | 1/2012 | Shimko | |
| 2013/0197647 | A1 | 8/2013 | Wolters et al. | |
| 2013/0211458 | A1 * | 8/2013 | Rezach | A61B 17/7038 606/264 |
| 2014/0236297 | A1 | 8/2014 | Iott et al. | |
| 2014/0277501 | A1 | 9/2014 | Northcutt et al. | |
| 2016/0317188 | A1 * | 11/2016 | Oglaza | A61B 17/1671 |
| 2017/0354513 | A1 | 12/2017 | Maglaras et al. | |
| 2018/0078384 | A1 | 3/2018 | Suddaby | |
| 2018/0296361 | A1 | 10/2018 | Butler et al. | |
| 2019/0053912 | A1 | 2/2019 | Suddaby | |
| 2019/0083275 | A1 | 3/2019 | Bell et al. | |
| 2019/0175224 | A1 | 6/2019 | Doubler et al. | |
| 2019/0274838 | A1 | 9/2019 | Manwill et al. | |
| 2020/0093603 | A1 | 3/2020 | Manwill et al. | |
| 2022/0142783 | A1 | 5/2022 | Ahmadi | |
| 2022/0168113 | A1 | 6/2022 | Ahmadi et al. | |
| 2023/0301695 | A1 | 9/2023 | Ahmadi et al. | |

FOREIGN PATENT DOCUMENTS

| | | | |
|---|---|---|---|
| EP | 3 463 202 | A1 | 4/2019 |
| JP | 2003-530915 | A | 10/2003 |
| JP | 2004-522469 | A | 7/2004 |
| JP | 2008-520269 | A | 6/2008 |
| JP | 2011-520580 | A | 7/2011 |
| JP | 2012-509157 | A | 4/2012 |
| JP | 2018-526152 | A | 9/2018 |
| WO | WO 01/54598 | A1 | 8/2001 |
| WO | WO 01/78798 | A1 | 10/2001 |
| WO | WO 02/38062 | A2 | 5/2002 |
| WO | WO 2006/051547 | A2 | 5/2006 |
| WO | WO 2009/147527 | A2 | 12/2009 |
| WO | WO 2010/059866 | A1 | 5/2010 |
| WO | WO 2012/162551 | A2 | 11/2012 |
| WO | WO 2012/162551 | A3 | 11/2012 |
| WO | WO 2016/112175 | A1 | 7/2016 |
| WO | WO2017/042366 | A1 | 3/2017 |
| WO | WO 2017/192525 | A1 | 11/2017 |
| WO | WO 2017/201371 | A1 | 11/2017 |
| WO | WO 2018/163056 | A1 | 9/2018 |

OTHER PUBLICATIONS

International Search Report and Written Opinion for International Application No. PCT/NL2019/050679, mailed Mar. 26, 2020.

International Preliminary Report on Patentability for International Application No. PCT/NL2019/050679, mailed May 6, 2021.

International Search Report and Written Opinion in International Application No. PCT/NL2020/050246, mailed Sep. 3, 2020.

International Preliminary Report on Patentability in International Application No. PCT/NL2020/050246, mailed Oct. 21, 2021.

International Search Report and Written Opinion for International Application No. PCT/NL2021/050446, mailed Oct. 1, 2021.

International Preliminary Report on Patentability in International Application No. PCT/NL2021/050446, mailed Feb. 9, 2023.

Office Action for Canadian Application No. 3,133,426, dated Jun. 2, 2023.

Office Action for Canadian Application No. 3,133,433, dated May 30, 2023.

Office Action for Japanese Application No. 2021-560279, mailed Sep. 1, 2023.

Patrick et al., Robust sacrificial polymer templates for 3D interconnected microvasculature in fiber-reinforced composites. Composites Part A: Applied Science and Manufacturing. Sep. 1, 2017;100:361-70.

Sun et al., Bio-CAD modeling and its applications in computer-aided tissue engineering. Computer-aided design. Sep. 15, 2005;37(11):1097-114.

Wang et al., Interlocking assembled 3D auxetic cellular structures. Materials & Design. Jun. 5, 2016;99:467-76.

* cited by examiner

ORTHOPAEDIC ASSEMBLIES, BONE FASTENERS, HEADS AND PACKAGES WITH SUCH ASSEMBLIES, SCREWS AND/OR HEAD, AS WELL AS METHODS FOR ASSEMBLING AN ORTHOPAEDIC ASSEMBLY

CROSS-REFERENCE TO RELATED APPLICATIONS

This application is a national stage filing under 35 U.S.C. § 371 of International Application Serial No. PCT/NL2022/050133, filed Mar. 10, 2022, which claims priority to Netherlands application number 2027748, filed Mar. 12, 2021, The entire contents of these applications are incorporated by reference in their entirety.

FIELD OF THE INVENTION

This invention relates to orthopaedic assemblies, bone fasteners, heads and packages with such assemblies, screws and/or head, as well as methods for assembling an orthopaedic assembly.

In particular, but not exclusively, the invention relates to such for a vertebral assemblies, e.g. with expandable vertebral implants, and screws, heads and packages for vertebral application.

Yet further examples of the invention relate to assemblies with pedicle fasteners which can be anchored to the pedicle, such as with screws to be driven into the pedicle and/or with tulip heads and packages, in particular, but not exclusively, to assemblies with poly-axial pedicle screws with tulip heads.

In particular, but not exclusively, the invention may be used in an assembly with an expandable, intra-vertebral implant which is to be anchored to the pedicle with a pedicle fastener.

BACKGROUND OF THE INVENTION

Bone fasteners with separate heads are known. For example, United States patent application publication 2011/0040336 discloses a thread-thru poly-axial pedicle screw system. In this known system, during manufacturing, the head is mounted on the pedicle screw by screwing the screw through a bottom part of a socket, unit the bottom part is at the upper end of the screw. Thereafter, an upper part is mounted on the bottom part such that a ball-socket joint is formed. The upper part can then be used to e.g. mount a rod onto the screw.

However, a disadvantage of such a system is that the system has to be prepared during manufacturing and it is not possible to select and mount the head with the screw already secured into the pedicle of the subject undergoing spinal surgery. As a consequence, when installing the screw, the head blocks free access to the upper end of the screw for a driving tool. Installing the bone fastener is therefore complicated and the access to the upper end with the driving tool bears a risk of damaging the head.

United States patent application publications US 2020/0323564 and US 2016/0206357 disclose pedicle screw systems with a head which can be mounted on the pedicle screw by a medical practitioner, after the pedicle screw has been appropriately secured into the pedicle of the subject. This head can be mounted on the pedicle screw by means of a snap-fit like connection. In such a case, the head is placed onto the pedicle screw and pushed towards the proximal end of the screw, until the snap-fit like connection is established between the head and the distal end of the screw. For the system disclosed in US 2020/0323564, the head is placed on the pedicle screw prior to placing the pedicle screw in the bone, whereas the system disclosed in US 2016/0206357 can be assembled with the screw already in the bone.

A disadvantage of these systems is that the snap-fit connection has to be very strong to avoid the head from separating post-surgery. There is therefore a significant resistance which has to be overcome to couple the head on the screw. Accordingly, the medical practitioner has to forcibly push the head onto the screw, and the associated force brings a risk of damaging the, often already fragile, bone of the subject undergoing surgery.

SUMMARY OF THE INVENTION

The present invention provides orthopaedic assemblies, bone fasteners, heads, packages, bone fixation systems and method of assembling a bone fastener as described in the accompanying claims.

Specific embodiments of the invention are set forth in the dependent claims.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

In the below, details will not be explained in any greater extent than that considered necessary for the understanding and appreciation of the underlying concepts of the present invention and in order not to obfuscate or distract from the teachings of the present invention.

Figure 1:
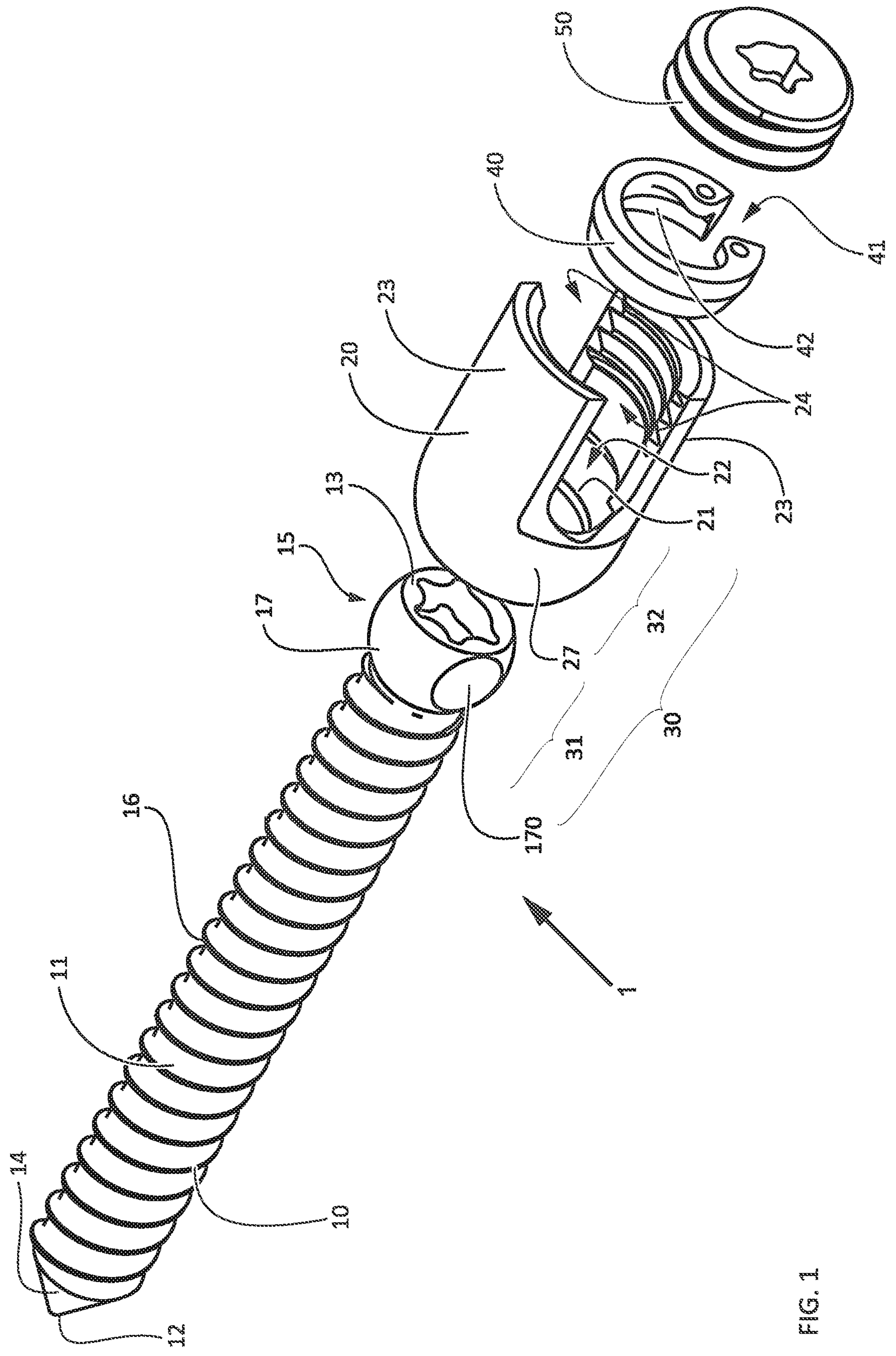
FIG. 1 schematically shows a perspective view of an example of an embodiment of a orthopaedic assembly in an unassembled state.
Figure 2:
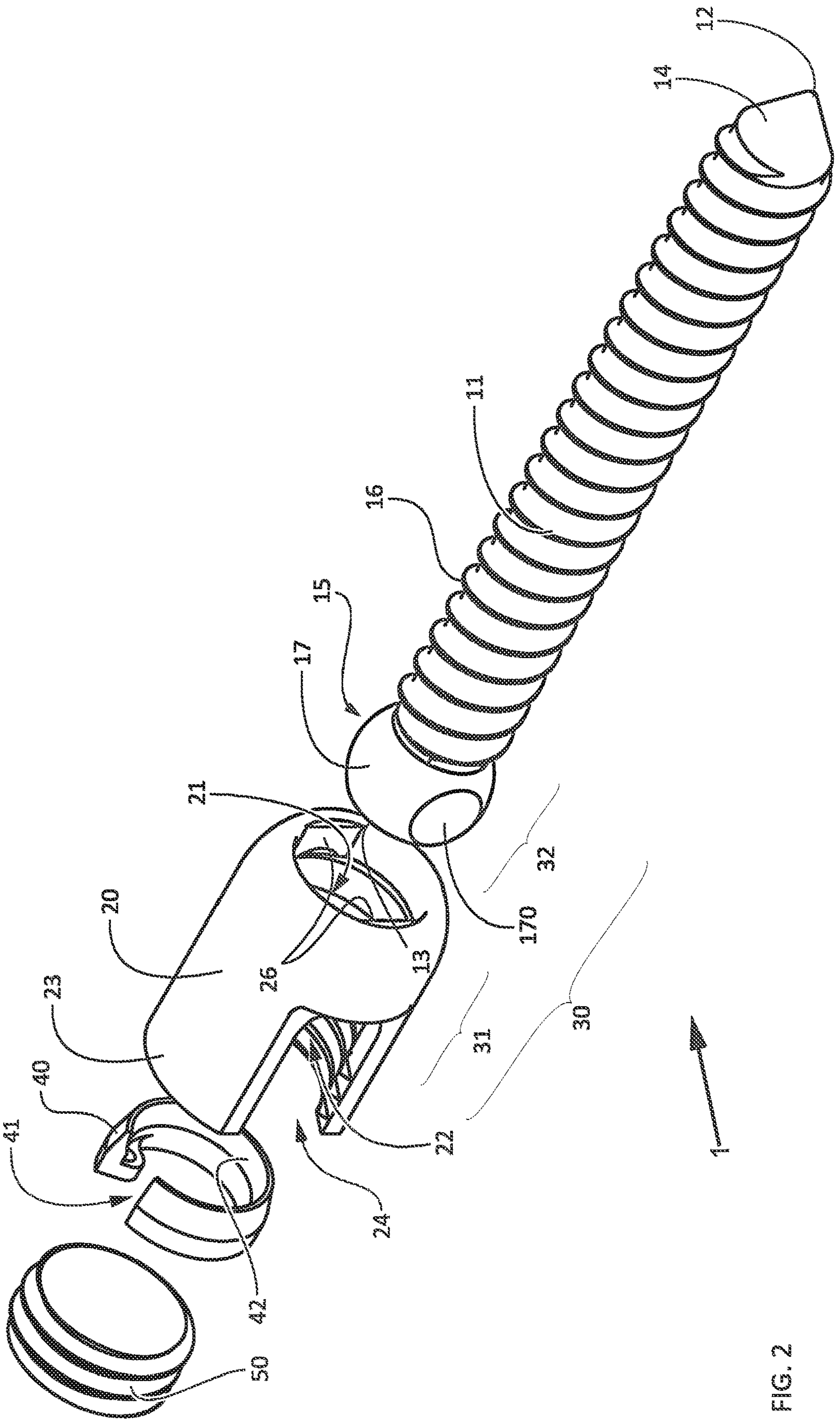
FIG. 2 schematically shows a perspective view of the example of FIG. 1 in the opposite direction.

Referring to the perspective views of FIGS. 1 and 2, as an example of an orthopaedic assembly 1, a bone screw assembly is shown therein in a disassembled state. The assembly 1 can be brought into an assembled state, for example by successively performing the operation illustrated in FIGS. 3-5 and the operation illustrated in FIGS. 6-8. The orthopaedic assembly 1 may be implemented, e.g. by appropriate dimensioning of the length, diameter, expansion ratio, and porosity, to be suitable for any type of bone of the mammalian body. The shown example is dimensioned to be placed into a vertebra of a human or non-human mammal, and more specifically into a pedicle, as is illustrated in FIGS. 20-27.

The example of orthopaedic assembly 1 shown in FIGS. 1-2 comprises a bone fastener 10 and a head 20. The bone fastener can for example be a vertebral bone fastener, such as lumbar, thoracic or sacral vertebral bone fastener.

Typical dimensions of the bone fastener 10 (although other sizes are possible as well depending on the bone in which the bone fastener is to be placed) can be a length of 10 mm or more, preferably of 15 mm or more, more preferably 16 mm or more. The length can be 70 mm or less, such as 50 mm or less, preferably 30 mm or less, more preferably 20 mm or less. A suitable currently preferred range for the length is a length between 30 and 60 mm. For example, the length can be between 35 mm and 55 mm, such as between 40 and 50 mm. A typical maximum diameter of the shaft can for example be less than 12 mm, such as less than 8 mm, such as 5 mm or less. Preferably, but not necessary, that diameter is 1 mm or more, such as 1.5 mm or more, 2.25 mm or more, such as 3 mm or more.

Typical dimensions of the head 20 (although other sizes are possible as well depending on the bone in which the head is to be anchored) can be a length of less than ⅓ of the length of the bone fastener, such as ¼ of the length, for instance between 8 and 18 mm, such as 10 mm. The diameter can for example be between 1½ to 4 times the diameter of the shaft 11 (excluding the thread, if present) of the bone fastener, such as 2 times the diameter thereof. A suitable currently preferred range for the length is a length between 12 and 16 mm and a diameter of between 9 and 14 mm as well.

The orthopaedic assembly 1 may comprise or consist of two separate, discrete parts: the bone fastener 10 and a head 20 which, in the disassembled state is freely movable relative to the bone fastener 10, and which can be mounted on the bone fastener 1. When mounted, the movement of the head 20 is restricted to a predetermined, limited range in all translational degrees freedom. Preferably, the head 20 has no freedom of motion in one, preferably two and most preferred three translational degrees of freedom. Said differently, although the head 20 may be implemented have some allowance to move translationally relative to the bone fastener, e.g. in the perpendicular to the axial direction of the shaft 11, currently most preferred is that the head 20 is completely fixated in position. Optionally, when mounted, the head 20 may retain one, two or three rotational degrees of motion in which the head is rotationally movable over a range, e.g. of less than 360 degrees, such as in case of a uniplanar or poly-axial mount for example.

Figure 19:
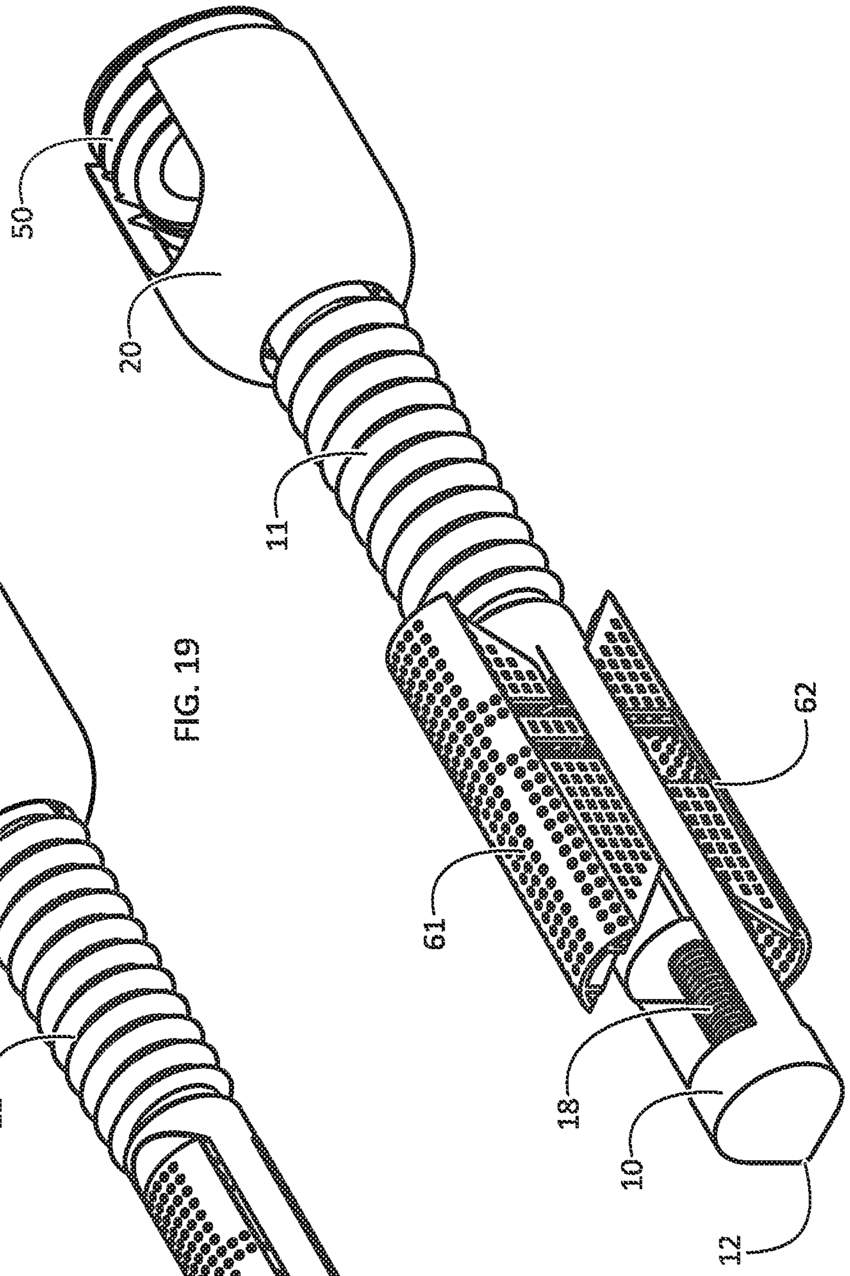
FIGS. 18 and 19 show a perspective view of a second example of a bone fastener, with a head similar to that of the first example but a different type of shaft.
Figure 18:
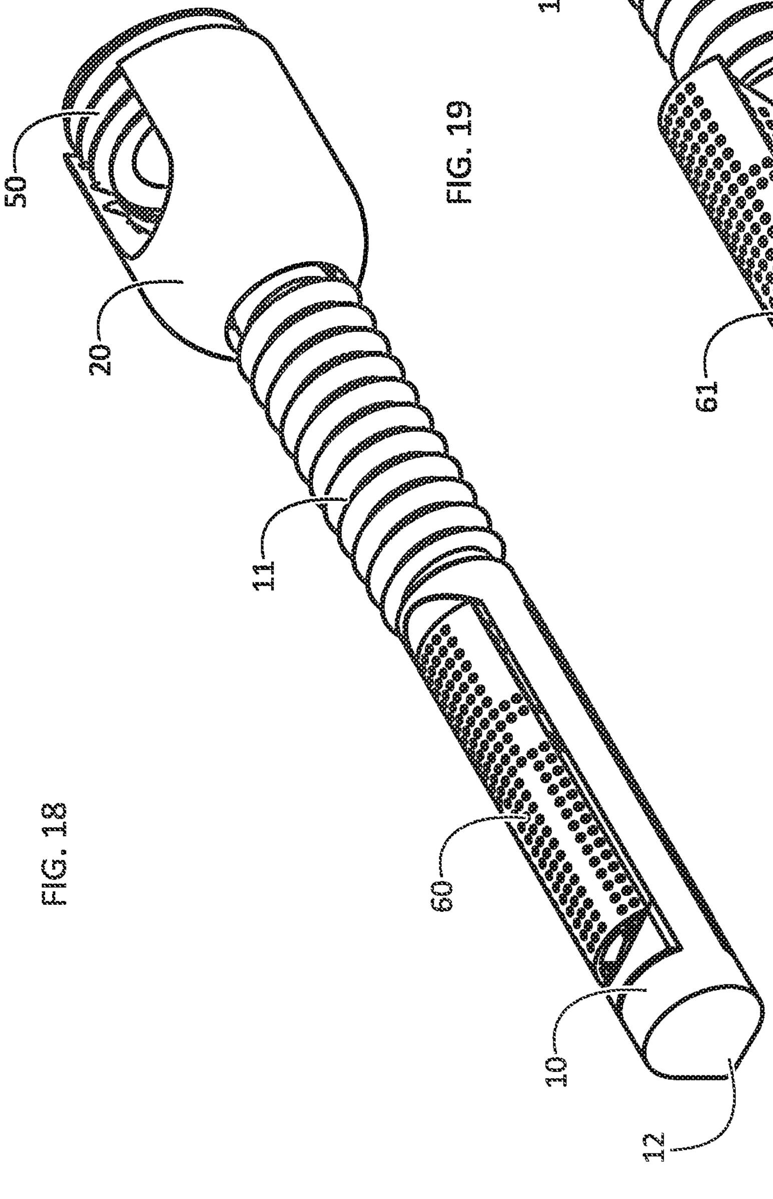

The assembly 1 may, as illustrated, additionally comprise other discrete parts, such as an insert 40 and a device fixation 50. In this example the bone fastener 10 is a single, integral part and the head 20 a single, integral part but alternatively each discrete part may be constructed from separate parts attached to each other. In the example of FIGS. 18 and 19, for example, the bone fastener 10 incorporates an expandable implant 60, with expandable parts 61,62, which can expand in a direction perpendicular to the axis of the bone fastener 10 to lift or support bone matter in that direction.

The bone fastener 10 comprises a shaft 11 for fastening the assembly 1 to another object. The shaft 11 may for example by used to fasten the assembly 1 in-vivo to a part of a bone of a subject with an orthopaedic condition, such as a bone fracture, for example a vertebral compression fracture. The orthopaedic condition may e.g. be one for which treatment comprises rigid or semi-rigid immobilisation of that part relative to e.g. another bone, such as a vertebra above or below the vertebra in which the bone fastener is placed. The immobilisation can e.g. be permanent, e.g. with a permanent interconnecting rod between the part and the bone or by fusing the part to bone with the use of a temporary interconnecting rod, such as a spinal rod in case of a vertebral assembly. Alternatively, the immobilisation can be temporary and the assembly 1 be a temporary immobilisation assembly, e.g. to relieve compressive pressure on a fractured vertebra, for instance.

The shaft has a proximal end 12 and a distal end 13. The proximal end 12 is shaped to form a tip 14 of the bone fastener. When affixed to a bone, the proximal end 12 with the tip 14 is the leading end of the bone fastener 10 which enters the bone first, while the distal end 13 is the trailing end which, depending on the specific implementation, after affixing the bone fastener 10 remains projecting out of the bone, is flush with the bone outer surface or is recessed into the bone, but less deep into the bone than the proximal end 12.

The bone fastener 10 is provided with a head post 15 which is located at the distal end 13. With the head post 15, the head 20 can be mounted to the bone fastener 10. To that end, the head and the head post 15 are each provided with a respective part 31,32 of a mount 30 for mounting the head 20 on the head post 15. More specifically, in this example the bone fastener 10 and the head 20 are in the non-assembled state mechanically seen independent from each other, and the mount 30 is an interlock which attaches and locks the head 20 onto the bone fastener 10. Said differently, when the head 20 is mounted, it is attached to the bone fastener 10. Said differently, the head cannot be removed from the head post with only a translational movement in one direction, i.e. for this example the free movement backwards in the direction opposite to the sliding direction is blocked by the locking.

Figure 15:
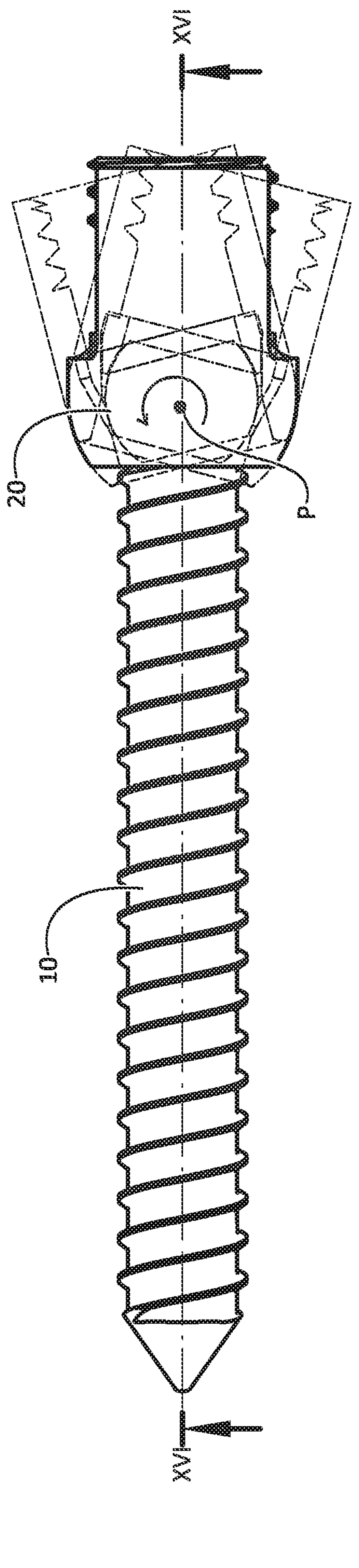
FIG. 15 schematically shows a side view of the assembled bone fastener.

The orientation of the head 20 can be changed in this example. The orientation can be changed by a rotational movement of the head 20 around one or more rotational axis extending perpendicular to the longitudinal axis, with or without rotation around the longitudinal axis of the bone fastener 10. When the head 20 is locked on the head post 15, the head 20 can e.g. be pivoted around a pivot point P, as indicated in FIG. 15 for instance. In this example the pivot point P is located in the head post 15. Furthermore, in this example the head 20 can be moved slightly further in the sliding direction, while the position is locked in the two other translational degrees of freedom. Thus, in this example a linear movement over a limited distance remains possible in the axial direction of the bone fastener 10. As explained below, the movement in the sliding direction may be completely blocked, either when mounting or thereafter. In this example, the movement is blocked by the insert 40 which confines the bulge 17 in the void without axial freedom of motion, but the movement of the head 20 in the sliding direction may be completely blocked in any other suitable manner.

The mount 30 has a head post side 31 and a head side 32 which cooperate to mount the head on the head post 15 and lock the head in position on the head post 15. As illustrated in FIGS. 3-8, a respective one of the sides 31,32, in this example the head side 32, is provided with a first lockable part 33 with an opening 21 in which a second lockable part 34 can be admitted. The second lockable part 34 is provided at the other side—in this example at the head post side 31. In the shown example, the opening 21 is provided in the head 20, which thus forms the first lockable part 33, in which, as an example of a second lockable part 34, a bulge 17 can be admitted, e.g. a ball-shaped bulge 17. The bulge 17 is part of the head post 15 of the bone fastener 10. Alternatively, the opening may be located in the head post and the head 20 may be provided with the second lockable part 34, to be admitted in the opening in the head post 15.

Figure 3:
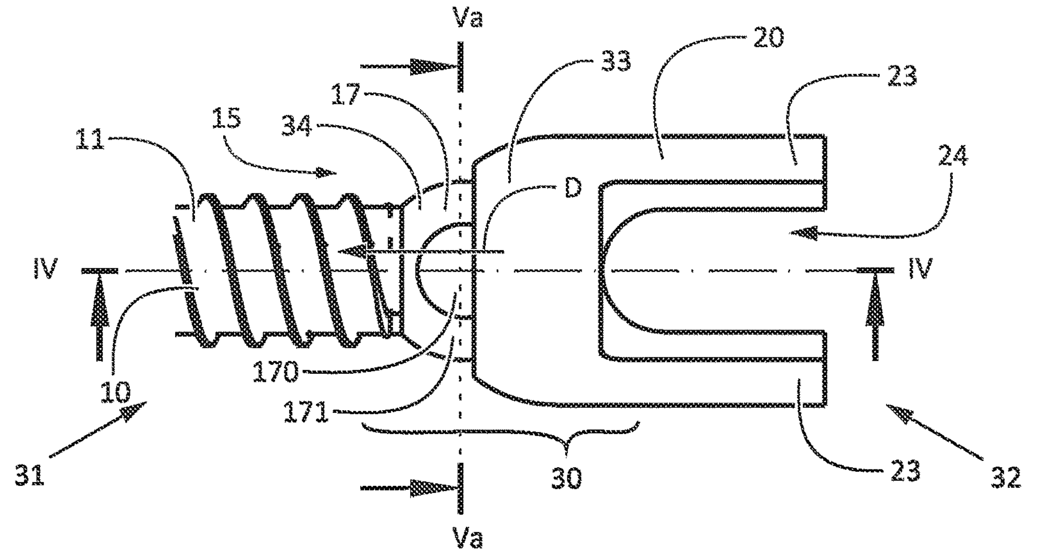
FIG. 3 schematically shows a partial side view of the example of FIG. 1 during assembling, illustrating the example of a mount in an engaged, but not-locked state.
Figure 4:
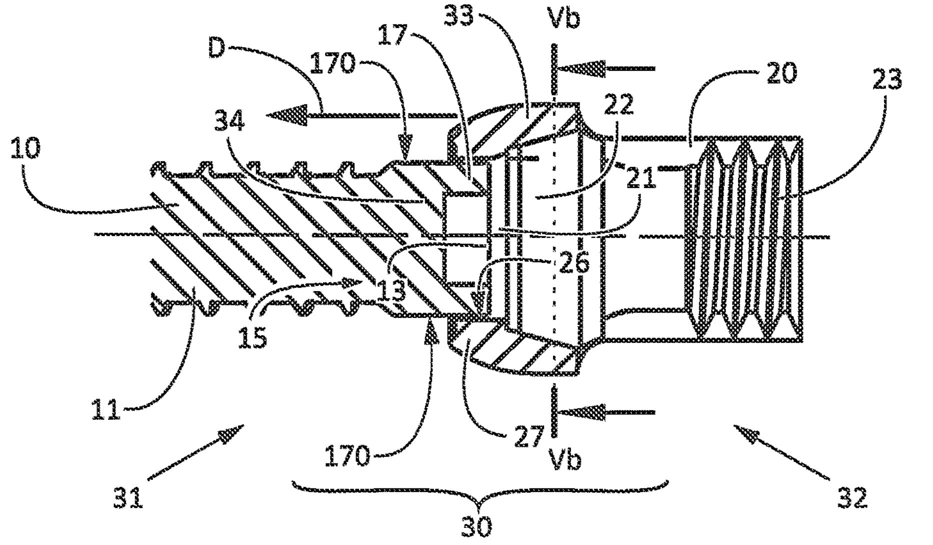
FIG. 4 schematically shows a sectional side view of the part of FIG. 3 taken along the line IV-IV in FIG. 3.
Figure 5:
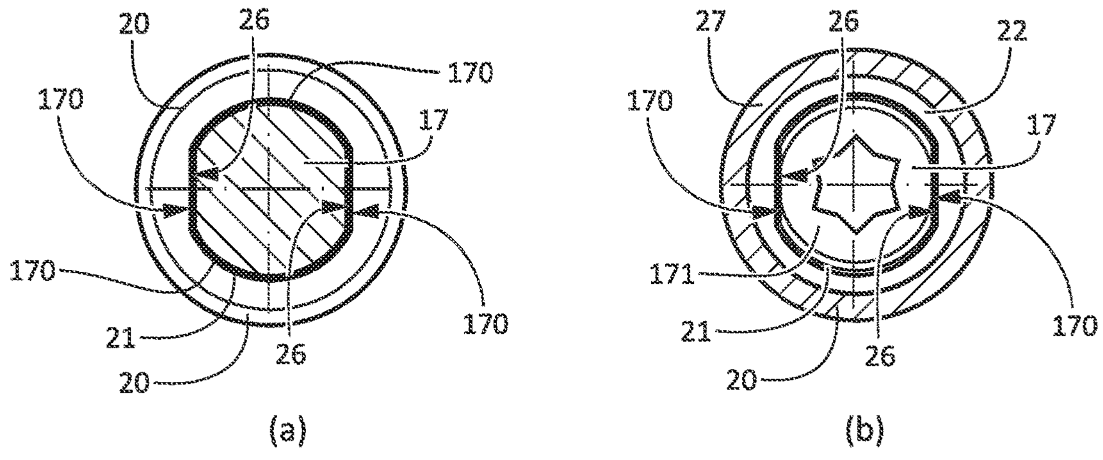
FIG. 5 schematically shows in (a) a cross-sectional view of the part of FIG. 3 taken along the line Va-Va in FIG. 3, and in (b) a cross-sectional view of the head part of FIG. 3 taken along the line Vb-Vb in FIG. 4.

The head 20 is mountable on the head post 15. The head 20 is mountable from the distal end side, by performing a sequence of predetermined translational and rotational movements. In this example, the sequence can be performed without deforming the interlocking parts, to establish a positive fit locking (also known as a "Formschuss"). Referring to FIGS. 3-5, in which the mount 30 is shown in an engaged, but not locked, state, mounting starts with moving the head 20 towards the head post 15, as indicated with arrow D in FIGS. 3 and 4, and thereby sliding the first lockable part 33 over the second lockable part 34 in a sliding direction. By the sliding, the second lockable part 34, in this example the bulge 17, is admitted into in the opening 21. The head 20 is thus placed on the bone fastener 10, and no longer freely movable but not yet locked either because the freedom of movement in the direction opposite to the sliding direction is unrestricted. Said differently, the head can still be removed from the head post with only a translational movement in one direction. The head 20 can thus still be removed from the head post 15 by simply sliding in the opposite direction, off the second lockable part 34, in which case in this example the bulge 17 is taken out of the opening 21. The movement is in the example in a distal-proximal direction from the distal end 13 towards the proximal end 12 but e.g. in case of a bone fastener with the head-mount 15 at a non-zero angle relative to the axis of the shaft 11, this may be in a different direction. In the shown example, the path along which the first lockable part 33 is slit is a straight path but this may alternatively be e.g. a helical path, with a translational-rotational movement of the head 20.

Figure 6:
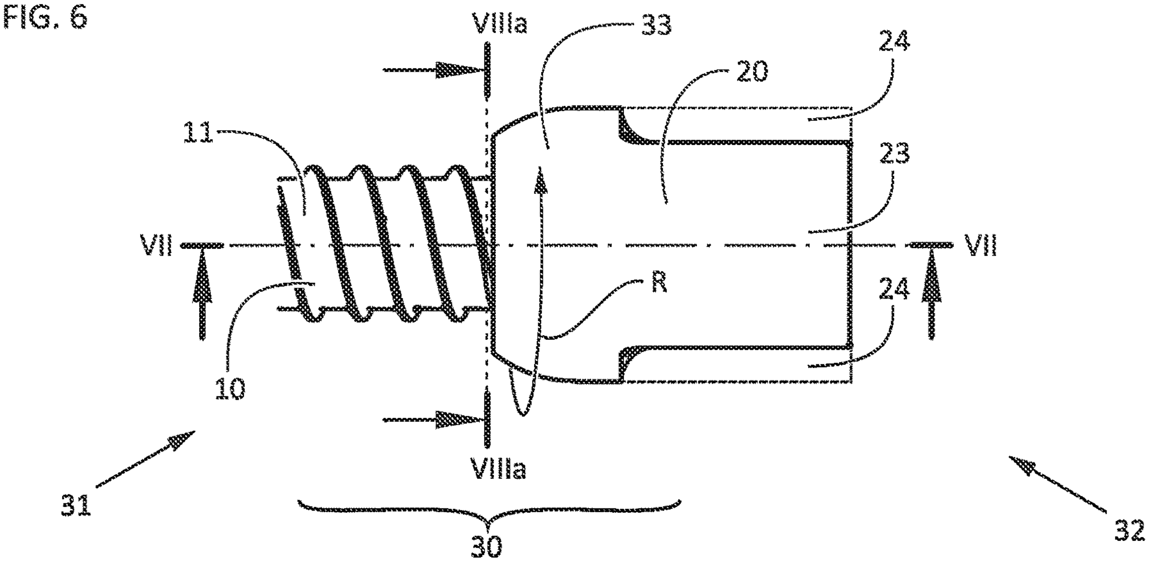
FIG. 6 schematically shows a partial side view of the example of FIG. 1 during assembling, after the state illustrated in FIG. 3, illustrating the mount in a locked state.
Figure 7:
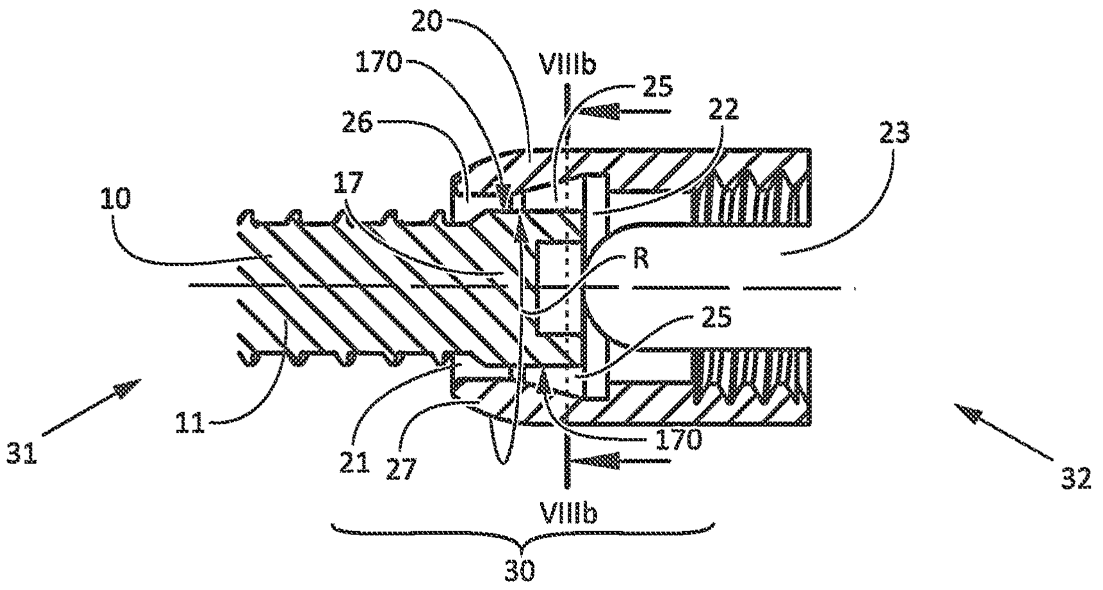
FIG. 7 schematically shows a sectional side view of the part of FIG. 6 taken along the line VII-VII in FIG. 3.
Figure 8:
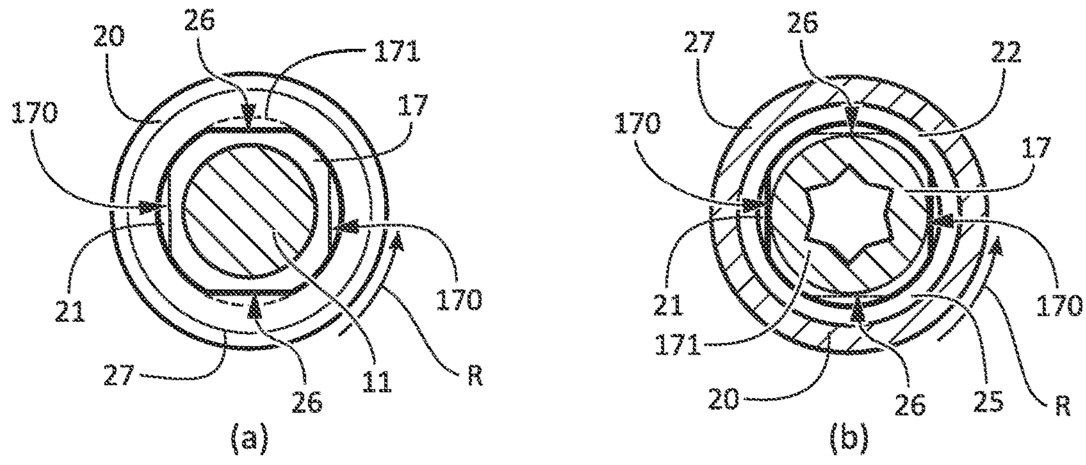
FIG. 8 schematically shows in (a) a cross-sectional view of the part of FIG. 6 taken along the line VIIIa-VIIIa in FIG. 6, and in (b) a cross-sectional view of the head part of FIG. 6 taken along the line VIIIb-VIIIb in FIG. 7.

As illustrated in FIGS. 6-8, which show the mount 30 in the locked state, which follows the engaged but not-locked state, once the head 20 placed on the head post 15 and the second lockable part 34 is admitted to a predetermined depth into the opening 21, the head 20 is lockable in position on the head post 15 by turning the head, as indicated with arrow R, around a rotational axis extending in the sliding direction. The axis may extend parallel to the sliding direction, which in this example is the distal-proximal direction. In this example, the head 20 can be turned without impairing rotation of the bone fastener 10, and when the head 20 is turned around the rotational axis the torque exerted on the head 20 does not impair a noticeable torsional deformation of the head. Thus, the head 20 is turned over a desired angular range around the rotational axis, from an unlocked orientation into a locked orientation. As a consequence, the second lockable part 34 can no longer be slid backwards, in the opposite direction, to taken out of the opening. In this example, the locking is a non-permanent fixation, in this example by establishing a positive fit locking in the opposite direction. Thus, second lockable part 34 can be slid backwards after translationally and or rotationally moving the second lockable part in other directions. Said differently, the head 20 is locked onto the head post 15 but can still be removed from the head post by a sequence of movements of the second lockable part, with the sequence comprising translational and/or rotational movements in directions other than the opposite direction.

The sliding can be performed with relatively little force, while at the same time the head 20 is mounted in a reliable manner by the locking. In addition, the turning movement is a relatively simple operation. Thus, mounting the head 20 on the bone fastener 10 is relatively simple and requires a small amount of force only.

The mount 30 further allows for example to assemble in-situ, during or shortly before surgery, a customized orthopaedic assembly with a limited risk of damage to the, often fragile, bone of the subject. For example, a specific head may be selected based on data directly obtained from the subject in-vivo during medical examination, such as type of fracture, bone density etc. instead of based on subsequent, secondary data of e.g. an X-ray image or the results of a bone biopsy.

In addition, the bone fastener can be placed in the bone first, without the head being present. In such a case the access, e.g. for a tool or for the hands of the medical practitioner, to the driving part of the bone fastener 10 is not spatially hindered by the head 20. Once the bone fastener is installed, the head may then be mounted on the head post. This allows to avoid a transfer to the head 20 of the, relatively high, forces required to screw the bone fastener 10 into the bone, and hence to limit or completely eliminate associated risk of damage to the head 20. In case the head post 15 is shaped to engage with a tool to exert a torque on the bone fastener, freedom of manoeuvring the tool to engage from the correct direction and at the right angle is not limited by the head 20, and the torque can be exerted with good precision. The head post may comprises an interface for engaging with such a tool. The head post 15 may for instance be provided with a hex head or other adapter for a driving tool.

Figure 13:
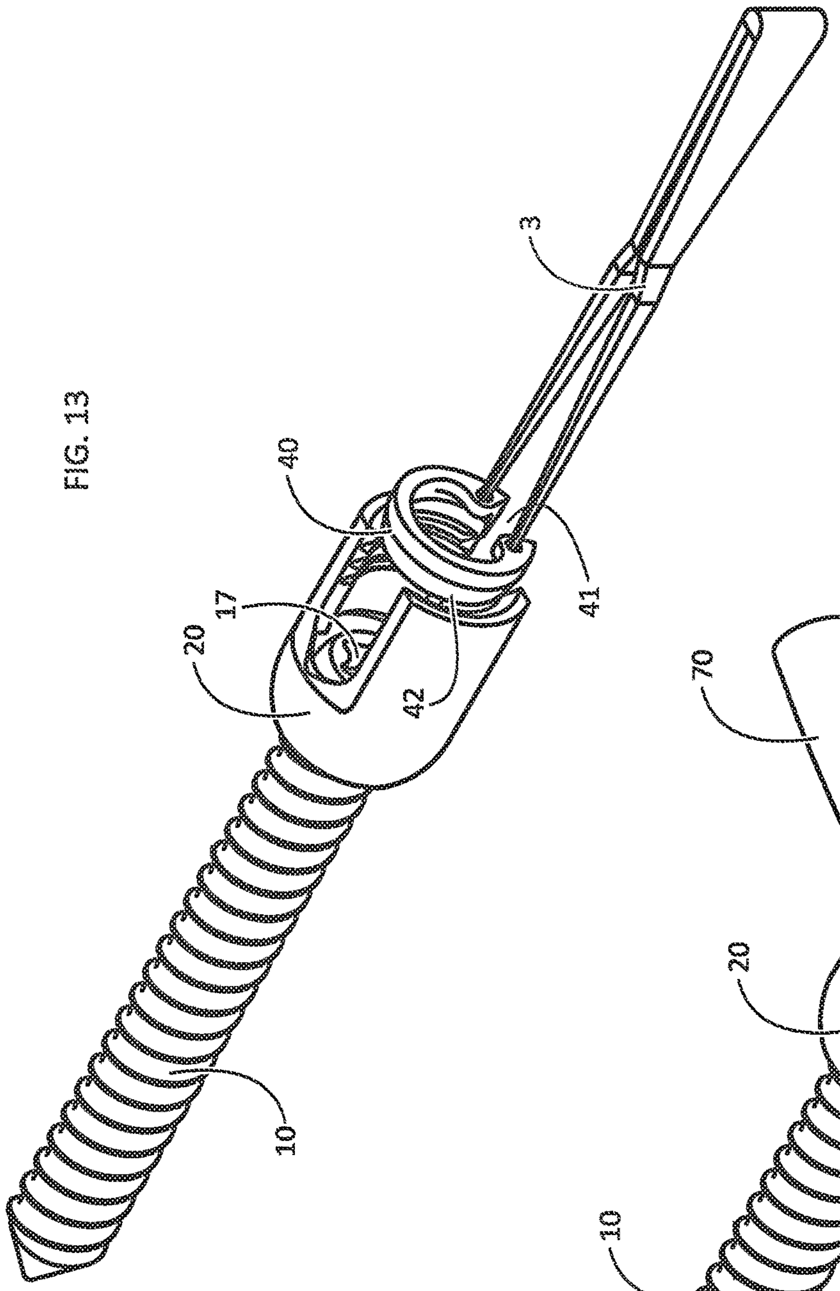
FIG. 13 schematically shows a perspective view of the example of FIG. 1 during further assembling, after the head has been mounted on the head post, to form a ball-joint between the head and the head post.

As can be seen in FIGS. 5(*b*) and 8(*b*), in these examples the interface is accessible with the tool after the first lockable part has been slid over the second lockable part and, optionally, after the head has been locked on the head post. More specifically, in these examples the tulip head does not obturate the access to the hex screw, and the tool can engage via the open side of the head, in this example the top end of the bore in the tulip head. Preferably, but not necessarily the interface remains accessible when the blocking element is correctly fixated in the first lockable part. For instance, as can be seen in FIG. 13, the insert 40 may have an annular shape with a central opening which leaves the access to the adaptor for the driving tool open.

The locking may be a permanent lock or be a releasable lock. In the shown example, after locking, the mount 30 can for instance be non-destructively unlocked to remove the head 20 from the head post 15 by performing an unlocking operation. In the example, this unlocking can be performed by moving, e.g. turning, the head in the direction opposite to that performed when locking the head 20 to return the mount 30 to the engaged, but not locked, state. This reinstates the motional freedom in the opposite direction and allows the second lockable part 34 to be taken op out the opening 21. Alternatively, the mount 30 may be implemented such that the unlocking operation is not the reverse of the locking but a different operation, e.g. to have an unlocked state which succeeds the locked state in the direction of turning. In such a case, for instance the mount may be unlocked by further turning the head until the head and the head post become unlocked.

The head post 15 and head 20 used in the assembly 1 may have any shape and be of any type suitable to perform the sliding and locking movements. For example, the mount 30 may comprise a pin projecting perpendicular to the distal-proximal direction and provided on the head post 15, and the opening 21 in the head 20 may be provided with a groove or slot in which the pin can be admitted to guide the movement of the head 20. For example, there may be an L-shaped groove or slot extending with a first leg in the sliding direction, e.g. parallel to the distal-proximal direction, and with a second leg perpendicular to the first leg or at an acute or obtuse angle, e.g. in a tangential direction around the axis of the bone fastener 10.

In the shown examples, the opening 21 and the bulge 17 are rotatable relative to each other to put the lockable parts 33, 34 in a locked or an unlocked position. The opening 21 has a non-circular cross-sectional shape perpendicular to the sliding direction. In this example, the cross-section is a circular disk with non-circular sides, more specifically flattened sides, but other shapes are also possible, for instance ellipsoid. As illustrated in FIG. 5, if the bone fastener 10 and the head are positioned co-axially and rotated around the coaxial axis relative to each other, at a certain angle or at an angle in a continuous range between two angles, they are in a fitting position. In the fitting position, the projection, in the sliding direction, of the bulge 17 onto the opening is fully overlapped by the cross-sectional shape and the bulge 17 fits into the opening 21. At another angle, the fastener 10 and the head 20 are in a non-fitting position. As illustrated in FIG. 8, in the non-fitting position at least a part of the projection is not overlapped by the cross-sectional shape and the bulge 17 does not fit into the opening 21.

The head 20 can in this example be mounted by positioning the bulge 17 and the opening 21 in the fitting position and sliding the bulge 17 into the opening 21 until the bulge 17 passes through the opening 21 and exits the opening 21 at the side opposite to the entrance of the opening 21. The head 20 can thereafter be locked onto the bone fastener 10 by bringing them into the non-fitting position, blocking removal of the bulge 17 out of the opening 21. In this example, this can be performed by simply rotating the head 20 or the bone fastener 10 around the co-axial axis, such that they transfer from the fitting position to the non-fitting position. The shaft 11 then extends through the opening 21 in this example, and projects out of the opening at the entrance side of the opening 21. The projecting part of the shaft 11, from the opening 21 to the tip 14 can have been anchored into the bone 100 before sliding the bulge 17 into the opening 21.

For each of the fitting and the non-fitting positions, the head 20 and head post 15 may be in that position at a single angle only or when at an angle within an angular range over which the head and screw are in the respective one of the locked state or the unlocked state. In respect, the angle is meant the angle over which the head and head post can be rotated relative to each other around the coaxial axis while respectively remaining fitting or non-fitting. Preferably, but not necessarily, the lockable parts 33,34 are in the non-fitting position not just at a single angle but over an angular range, with a predetermined subrange e.g. of at least 5 degrees and/or not more than 355 degrees, over which the parts of the projection not overlapping with the cross-sectional shape are at a maximum, and the head and head post are in a completely locked position. This subrange allows to still adapt the orientation of the head 20 after mounting and locking.

For example the orientation may be adapted to attach a medical device on the head 20 in a desired position, without risk of the head 20 accidently coming loose from the head post 15. The medical device may e.g. be a mechanical device, such as for temporarily or permanently immobilizing the part of the bone to which the fastener 10 is fixated, and in which the fastener 10 is placed, to another (part of) bone by mechanically connecting the fastener 10 to that other (part of) bone. For example, after mounting the head 20, a rod 70, such as a spinal fixation rod, may be fixated to the head 20, as explained below in more detail and illustrated in FIGS. 13 and 14. By rotating the head 20, while staying within the subrange, a desired orientation of the rod may be prepared. For example, the rod may be oriented to point into a selected direction after fixating to the head 20 or the head 20 may be positioned such that upon fixation onto the head 20 the rod obtains that orientation. For example, the rod may be oriented to span the distance to another head of another screw anchored in another bone segment and couple the screws to each other, such as for a spinal fixation of two or more spinal segments for instance. In the shown example, the range of the fitting position is a very narrow range, of less than 1 degree, and preferably a specific angular value. The range of the non-fitting position, as well as the subrange of the locked position, is preferably a larger range than the narrow range. Thereby, when mounting the head 20 a medical practitioner can from the orientation of the head 20 derive relatively easily how the head post 15 is oriented.

In the shown example, for each of the cross-sectional shape and the projection, the respective circumference is formed by spaced apart elliptical, more specifically circular, arcs which are connected by chords of the ellipse or circle of which the arc is a part. Said differently, each of the cross-sectional shape and the projection is an elliptical or circular segment defined by two chords, which in this example are parallel. As illustrated in FIG. 5, in this example in the fitting position the cross-sectional shape and the projection almost coincide. As illustrated with the dashed lines in FIG. 8, in the shown example, in the non-fitting position, circular segments of the projection are not over-lapped by the cross-sectional shape, and more specifically in the locked position the union of the projection and the cross-sectional shape results in a complete circle.

As can best be seen in FIG. 1, the bulge 17 is in this example an ellipsoid, more specifically a spherical, segment 171. Said differently, the second lockable part 34 has a ball shape with one or more flattened sides 170 extending parallel to the sliding direction. The opening 21 is a horizontal cylindrical segment, as can best be seen in FIG. 2. Said differently, the opening has a round, non-circular cross-section perpendicular to the distal-proximal direction. The opening has in this example flattened sides 26 parallel to the sliding direction.

The cylinder segment and the ellipsoid segment provide robust shapes which are not easily damaged and can be implemented such that they are not sharps. However, other shapes may be suitable as well, such as for example star shaped cross-sections and projections, cross-shaped cross-sections and projections or other non-circular shapes. Also, the cross-sectional shape and the projection have in the example the same geometrical shape and dimensions, but they may differ, for example, the projection may be elliptical and the cross-sectional shape be rectangular, as an example or the dimensions may differ.

In this example, the cylindrical segment is that of a circle cylinder. The cutting planes forming the respective flattened sides 26, 170 of the ellipsoid segment and the cylinder segment, are parallel, in this example the same, when the opening 21 and the bulge 17 are co-axially aligned. In this respect, the diameter of the cylinder in the direction parallel to the flattened sides 26 may be equal or larger than the longest diameter of the ellipsoid, and the distance between the flattened sides 26 of the cylinder be smaller than the longest diameter of the ellipsoid. In such a case, when the ellipsoid is oriented with the main axis of its ellipse non-parallel to the flattened sides 26 of the cylinder, the mount is in the non-fitting position, whereas when the ellipse is oriented with the main axis parallel to the flattened sides 26, the mount is in the fitting position. The distance between the flattened sides 26,170 and the differences in diameter determine the angular ranges of the locking position and may therefore be chosen as is deemed suitable for the specific implementation. In the shown example, as illustrated in FIG. 8(*b*) the orientation in the locking position of the flattened sides 26 of the cylinder and the flattened sides 170 of the ellipsoids can be visually perceived, and accordingly the orientation of the head 20 be adjusted without requiring additional equipment while still staying in the subrange of angles over which the head is securely locked.

As can best be seen in FIG. 5*a*, when the bulge 17 is admitted into the opening there is a tight fit between the opening and the bulge 17, preferably a non-interference fit, such as a location fit or a transition fit. In addition, the bulge 17 and the opening 21 both have a non-circular cross section perpendicular to the sliding direction, which in this figure is the distal-proximal direction. Accordingly, the bulge 17 acts as a guide for the movement of the head 20 along a predetermined guide path. In this example, the guide path is straight and inhibits rotation of the head 20 around the axis of the bone fastener 10 when sliding the head 20 onto the head post 15. Alternatively, the opening 21 and/or bulge 17 may be shaped such that free rotation over a limited range is possible or the guide path be a turned path such that upon sliding onto the head post 15, the head 20 is forced to rotate along the axis of the bone fastener when progressing over the turned path, for example.

As illustrated in FIG. 6-8, in the shown example, the opening 21 mouths into a void 22. In this example the void 22 is a space inside the first lockable part 33, the walls of the space being defined by parts of the part 33, of but alternatively the void 22 may be the exterior of the first lockable part 33. The void is in this example separated from the outside world by the first lockable part 33, and open at an open side opposite to the side where the opening 21 mouths. The void has a shape which differs from that of the opening. More specifically, the bulge 17 fits into the void both in an initial orientation corresponding to the orientation when exiting the opening 21 and entering the void 22, the mount thus being in the engaged, but not locked, state, as well as a locked orientation where the bulge 17 has been rotated relative to the initial orientation around an axis parallel to the sliding direction to put the mount 30 in the locked state. As will be apparent from FIGS. 7 and 8, in this example, when the bulge 17 is completely admitted in the void, the second lockable part 34 is rotatable over a predetermined range, here 360 degrees, around the axis.

In this example, the space constituting void 22 is a bore in the head 20, with a diameter equal to or larger than the largest diameter of bulge 17 in the direction perpendicular to the sliding direction. Thus, the bulge 17 fits into the bore in both the fitting and the non-fitting orientation of the head 20 relative to the bone fastener 10. Although the bore may have another shape, in this example the bore has a cylindrical shape. As shown, the bore can be tapered towards the opening 21, with the narrow side transitioning into the opening 21. The bore and the opening 21 are co-axially aligned, but alternatively for example the axis of the bore may be off-set in the radial direction relative to the rotational axis of the bone fastener 10 and/or the opening 21.

The opening 21 mouths into the bottom of the bore. The bottom of the bore is curved and shaped as a bowl such that the spherical surface of the bulge 17 can slide over the curved surface thereof. The curved surface defines the bottom side of a cage in which the bulge 17 is confined in the locked state, and which defines a pivot point for the bulge 17. As explained below, the cage has a running surface over which a contact surface of the bulge 17 is rotationally movable around a pivot axis through the pivot point P. At the opposite side of the bulge 17, e.g. an insert 40 can be placed with a curved surface 42 facing the bulge 17, which defines the top side of the cage. Together with the bulge 17, the cage can form a ball-joint of which the cage is the socket and the bulge 17 for example the ball.

The orthopaedic assembly may comprise a blocking element for blocking the bulge from exiting the void at the open side. As illustrated in FIG. 13, for example an insert 40 may be placed in the bore which blocks the bulge from passing further into the bore. In this example, when the head 20 is mounted on the head post 15, the second lockable part 34 projects out of the opening 21 into the void 22. The insert 40 can be placed into the bore to project into the bore in a direction perpendicular to the sliding direction, and in this example projects in the radial direction towards the axis. This projection reduces the diameter of the bore at the location of the insert to be less than the diameter of the bulge 17, thereby blocking the bulge 17.

In this example, the insert 40 is an internal circlip, that is a split ring of which in an uncompressed state a gap 41, which may also be referred to as a split, is present between open ends of the ring. As illustrated in FIG. 13, a tool 3, in this example circlips pliers, may engage with the ends of the circlips at the opposite sides of the gap 41 of the horseshoe-shaped circlips, to bring the ends closer to each other and resiliently compress the ring, thereby reducing the gap 41 and reducing the diameter of the insert to fit into the bore. When the insert 40 is placed to abut to the bulge 17, the tool may then be removed to release the insert 40 and allow this to decompress, such that it presses in the radial direction of the bore against the wall of the bore and is fixated in the axial direction. To keep the insert 40 in position in the axial direction, in the shown example the diameter of the bore has a stepped profile, such that the insert is positioned in a part of the bore with a wider diameter and comes to abut in the axial direction against a step where the diameter discontinuously is reduced and smaller than the decompressed diameter of the insert 40, the step being present between the open side and the insert 40.

Figure 16:
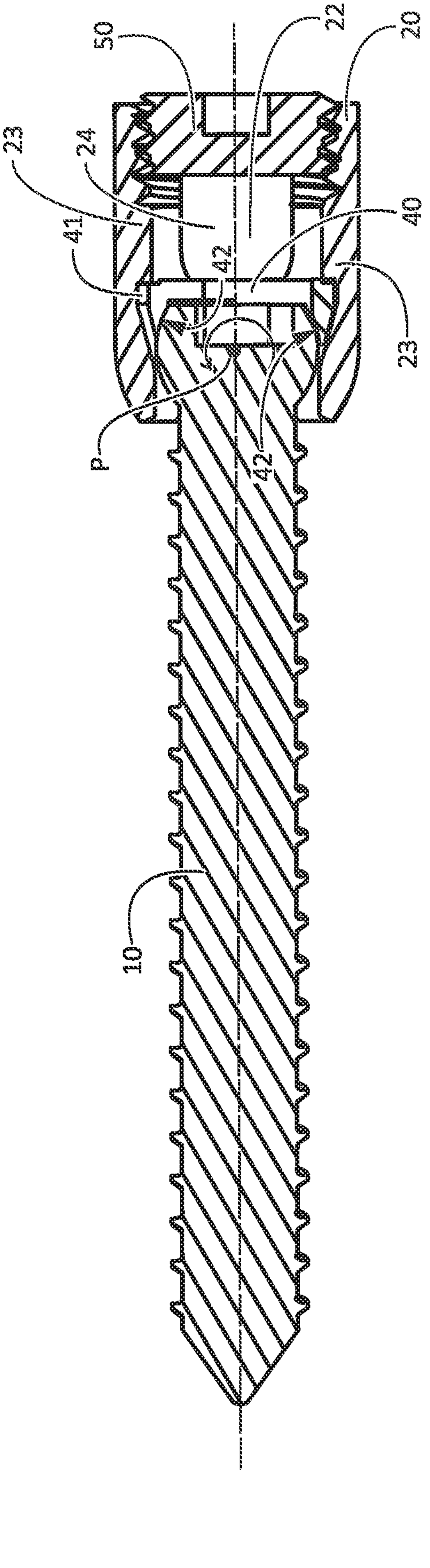
FIG. 16 schematically shows a sectional side view of the example of FIG. 15.
Figure 17:
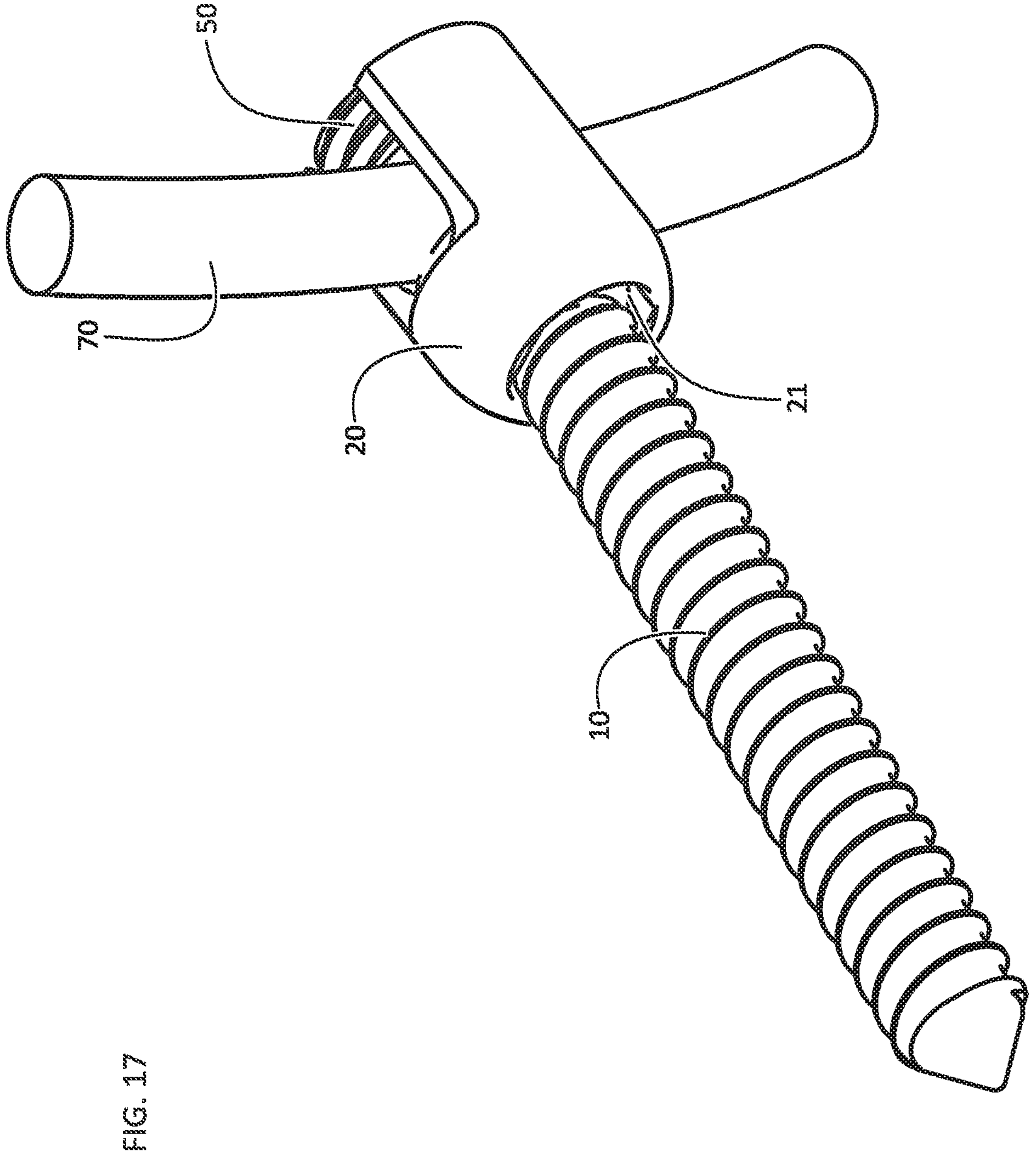
FIG. 17 schematically shows a perspective view of the example of FIG. 15 with a medical device mounted on the head.

In the shown example, the insert 40 further forms the top side of the afore mentioned cage. As is best seen in FIG. 16 in this example, the insert 40 has a concave side 42 with a shape complementary to the shape of the second lockable part, for admitting the side of the second lockable part facing into the opening. Like the bottom part of the cage, the concave side 42 of the insert 40 is curved around a pivot point P.

The second lockable part 34 can rotate in one or more direction around the pivot point P when the distal end of the second lockable part 34 is admitted in the concave side 42 of the insert. More specifically, as illustrated in FIG. 8 (*b*), in the locked state an annular gap 25 is present between the second lockable part 34 and the first locking 33 part at a projecting side of the second lockable part 34 facing away from the opening 21. As shown in FIG. 7, when the bulge 17 is in the void 22, the annular gap 25 encloses the bulge 17 in the circumferential direction around the axis of the bore. The insert 40 can be placed to fit into the annular gap 25, oriented co-axially therewith. When the bulge 17 extends through the disk enclosed by the annular gap, in which the insert is placed, the bulge 17 abuts to the concave side 42, and the curvature of the concave side 42 defines the pivot point P for the bulge 17, as illustrated in FIG. 16. In this example, when the circlips 40 is positioned in the annular gap 25, the concave side 42 abuts to the ellipsoid, e.g. spherical, surface of the bulge 17 and forms with the bottom part of the cage a running surface over which the ellipsoid surface of the bulge 17 can slide.

Accordingly, in the locked state the bone fastener 10 can be rotated around a rotational axis relative to the head mount 20 through the pivot point, in this example without translational movement. In the shown example the assembly is a poly-axial screw assembly and this rotational axis can be freely chosen. In another example, the freedom of rotation around the axis of the shaft 11 is blocked, and only the angle between the bone fastener 10 and the head mount 20 can be adjusted by rotation around any axis perpendicular to the axis of the shaft 11, as illustrated in FIG. 15. In another example, the assembly is a uniplanar screw assembly and the angle between the bone fastener 10 and the head mount 20 can only be adjusted by rotation around a single, predetermined axis perpendicular to the axis of the shaft 11.

The part of the second lockable part 34, in this example the shaft 11, admitted in the opening 21 in the locked position has a smaller diameter than the opening 21 in all radial directions. The bone fastener 10 thus be rotated around any axis through the pivot point over the angular range defined by the angles at which that part of the second lockable part 34 comes to abut to the opening 21.

In this example, the second lockable part 34 is located on the bone fastener 10. The bulge 17 forms a leading end of the second lockable part 34, for entering the opening 21 first, and the second lockable part 34 has a trailing section connected to the bulge 17, in this example the shaft 11. The trailing section is, when the bulge is completely admitted in the void 22, pivotable around a pivot axis in the void 22 which extends through a predetermined pivot point P. The shaft 11 has in one or more direction a diameter smaller than the maximum diameter $d_{max}$ of the opening 21 and equal to or smaller than the minimum diameter $d_{min}$. The shaft 11 thus fits into the opening 21 in the non-fitting position and is movable in the directions where the diameter of the shaft is smaller than that of the opening, in this example in all radial directions can be seen in FIG. 8. When the bulge 17 is located in the void 22, the pivot axis of the bulge 17 forms the rotational axis for the shaft 11. The bone fastener 10 thus has the rotational degrees of freedom determined by the pivot axis and the directions in which the shaft 11 can move in the opening 21, with the range of rotational freedom being set by the angular range over which the shaft 11 can be rotated in the opening.

Alternatively, the mount may be implemented such that in the locked state the head 20 is unmovable relative to the screw 10, i.e. a mono-axial assembly, or only rotatably movable in a single plane, i.e. a uniplanar assembly. For example, the shaft 11 and/part of the bone fastener 10 extending in the opening 21 in the locked state may be shaped such that in some radial directions the rotation is blocked in the locked state, e.g. because the diameters are equal in these radial directions.

The bone fastener 10 may be any type of bone fastener suitable to be anchored into the specific type of bone. The bone fastener 10 may for example be a cancellous bone fastener, a cortical bone fastener or a screw for both cancellous and cortical bone. The bone fastener may be a bone screw, such as a vertebral screw, such as in this example a pedicle screw for fixating an extra-osseous device, such as mounted on the head, located at the distal end onto the bone. The extra-osseous device remains extraneous from the bone but may e.g. be flush or recessed. Additionally or alternatively, the bone fastener may be a bone anchor for anchoring an intra-osseous orthopaedic device to be placed into the bone itself, e.g. for an expandable implant that provides support to the bone to withstand compressive forces acting on the bone. The intra-osseous device may e.g. be a device located between the distal end and the proximal end a device.

In this example, the bone fastener 10 has a pointed tip 14, more specific a cone with the apex forming the proximal end 12 of the bone fastener. The tip 14 is connected to the head post 15 by the shaft 11. However, the bone fastener 10 may alternatively be without a pointed tip 14, and for example have a shaft 11 which extends up to the proximal end 12 and which e.g. has a flat, disc-shaped proximal side or the shaft 11 be tapered towards the proximal end into a point.

In the shown example, the bone fastener 10 is a monolithic body made in one piece, but alternatively it may be composed of several separate pieces which are e.g. screwed onto each other. For example, the shaft 11 may be a separate piece which is screwed or otherwise fixated onto the head post 15. As shown, in a currently preferred example, the bone fastener 10 is a monolithic, non-porous structure, but alternatively parts of the bone fastener 10 may have a porous outside to enhance osseointegration of the bone fastener 10 and/or partially or completely porous inside which can be incorporated into the bone by osseo-incorporation. In an example, the shaft 11 may be such a porous part, while the head post 15 may be a non-porous structure.

The shaft 11 may be of any type and have any shape suitable to anchor the bone fastener into the bone. The shaft 11 may be an elongate body, e.g. rounded or not rounded. In this example, the shaft 11 has for example rounded shape, more specifically a cylindrical shape, and although in this example this is a circular cylindrical shape, other rounded cylindrical shapes such as elliptical cylinders may also be suitable, as well as other rounded shapes such as a cuboid (or other polyhedrons) with chamfered lateral edges, for instance. The shaft may, as in this example, have a longitudinal axis parallel to the distal-proximal direction, around which the shaft 11 is rotatable to drive this into the bone, for example.

The diameter of the shaft 11 can be constant. In this example, the diameter is constant over the whole length. As shown, the cross-section of the shaft may be constant from the proximal end to the head post 15. Alternatively, the diameter may vary, monotonically or not, (e.g. tapers towards the proximal end 12) along the longitudinal direction, either locally or over the whole length.

The outside of the shaft 11 can have a friction enhancing profile for holding the assembly 1 in the bone 10. The shaft 11 can for example have an outer surface extending in the lateral direction, which may, seen in the longitudinal and/or circumferential direction be unprofiled, partially profiled or completely profiled. In this example, the outer surface has a profiled area where the outer surface is provided with a profile that extends circumferentially around the shaft 11 and extends in the lateral direction from the proximal end 12 up to up to the distal end 13. Alternatively or additionally, one or more unprofiled areas may be present. E.g. the shaft may be completely smooth and unprofiled, or partially unprofiled. For example, the distance between the head post and the thread 16 may be unprofiled, such as a shoulder with a diameter smaller than the head post and smaller, equal to or larger than the diameter of the thread 16.

In this example, the profiled part is a threaded part provided with the thread 16 but depending on the specific implementation the profile may for instance be ribbed or fluted. Also, in this example the shaft 11 is fully threaded, i.e. the thread extends from the tip 14 to the head post 15, and thus forms a shank of a fully threaded screw, but is will be apparent that alternatively the shaft 11 may be partially threaded, e.g. in case of a cancellous lag screw, or non-threaded in which has the fastener 10 can be referred to as a pin or as a peg which is attached to the bone by an interference fit.

Alternatively, or additionally, an unprofiled area may be present between the thread 16 and the proximal end 12. In the example of FIG. 18-19, the thread 16 is spaced from the proximal end 12, for example. The length between the thread 16 and the proximal end 12 does not engage with the thread in the bone but is occupied by a device, in this example an expandable implant 60, which does not anchor into the bone but provides support to a part of the bone. It will be apparent that instead of expandable implant other (orthopaedic) devices may be present, and for example that the unprofiled part of the shaft 11 may serve as e.g. an axle for another device, may serve to hold the device in position relative to the distal-proximal direction for example, or may be shaped as an awl.

Figure 21:
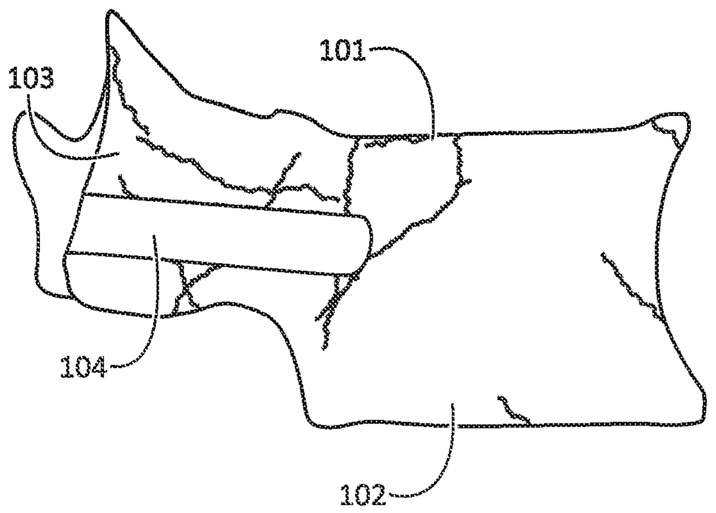
FIG. 21-24 show side views of a bone, during successive stages of an example of a procedure of fixating the example of FIG. 1 into the bone.
Figure 22:
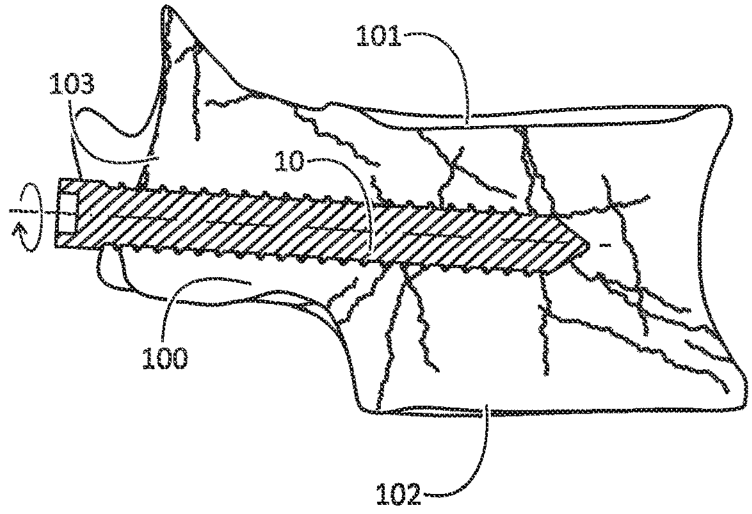

The tread 16 may be sufficiently sharp and rigid that upon rotational insertion of the bone fastener 10 in a pre-drilled cannula in the bone, the shaft 11 forms a thread in the cannula, complementary to the thread 16 of the body, in the cannula, and the shaft 11 may thus be a thread forming screw body. In the shown example, this screw body is not self-tapping and accordingly is inserted in a pre-drilled cannula 104, as illustrated in FIG. 21-22. However, alternatively the shaft 11 may be self-tapping and e.g. at the proximal end 12 be provided with a sharp point, and along the outside surface be provided with a self-tapping thread which extends from the point at the proximal end 12 towards the distal end 13.

Figure 14:
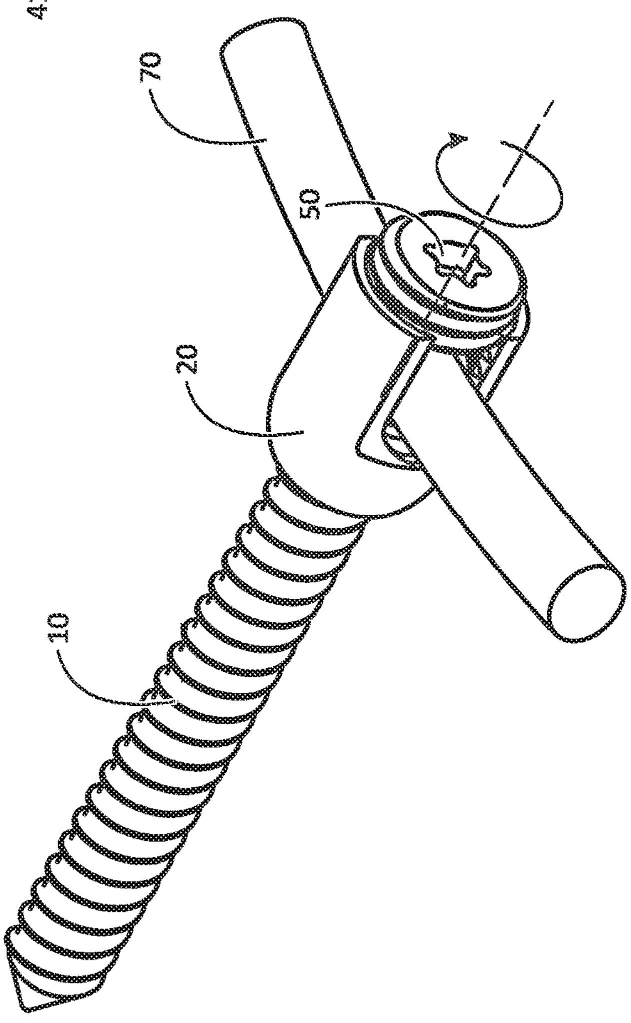
FIG. 14 schematically shows a perspective view of the example of FIG. 1 after assembling, illustrating mounting a medical device on the head of the bone fastener.

The head 20 may be any type of head. In this example, the head has a U-shaped cross section, with the head body 27 forming the base of the U, and the walls of the bore forming the legs. The head 20 may, as shown, be a tulip but other types of heads may likewise be used. As shown, the tulip has two or more opposing tabs 23 extending from the base, in the axial direction of the bore, towards the top of the head. The tabs 23 are spaced by slots 24. In the slots 24 a spinal rod or other object can be received, to be fixated in the tulip by a device fixation 50. As illustrated in FIG. 14 for instance, the tulip may be provided with internal threads to receive as a device fixation 50 a set screw to anchor or fix the rod 70 in the tulip. For instance, the top end of the bore may be provided with these threads, to fixate the rod 70 between the insert 40 and the device fixation 50 and block the rod 70 from slipping through the slots 24, in the longitudinal direction of the rod 70, In this example, the walls of the bore form the tabs 23, with the slots 24 extending in the axial direction from the top of the head 20 towards the bottom, but not beyond the opening 21. As can be seen in FIGS. 4 and 7, the slots 24 can terminate at a distance from the opening 21, and in these FIGs. extend up to the top side of the cage formed by the insert 40. The slots 24 thus terminate at the upper side of the annular space 25. The body 27 thus forms a housing for the head post 15, and for the pivot joint between the head 20 and the bone fastener 10. The housing encloses these parts circumferentially from the entrance of the opening 21 up to the top-side of the annular space 25 and reduces the risk of damaging the pivot joint when installing a rod 70.

As mentioned above, between the head 20 and the head post 15 a uniplanar or poly-axial pivot joint may be established. To keep the head post 15 in the tulip, in this example, the tulip has a lower receptacle that operates as a socket for housing an upper retainer ring which interrupts the movement of the bulge in the axial direction. That is, in this example, the bulge after having entered the bore from the opening cannot pass beyond the upper retainer ring More specifically, the insert can be placed in the body through the head 20 as explained above with reference to FIG. 13. Alternatively, e.g., the bore may be threaded and the assembly 1 may comprise set screw with a socket-shaped side which can be screwed into the threaded bore with the socket-shaped side facing the bulge 17, e.g. from the top of the tulip to a position below the slots 24, until it abuts to the bulge 17 and thus blocks the bulge 17 from moving axially further towards the top of the tulip.

Referring to FIG. 14, the orthopaedic assembly may comprise a fixation for fixating a medical device onto the head 20. In this example, the device fixation 50 comprises a locking nut for clamping the medical device in a receiving recess of the head 20. In this example, the receiving recess is the longitudinal extension of the void 22, from the part in which the second lockable part 34 is received up to the top of the head 20. The walls of the receiving recess are formed by the tabs 23 extending in the proximal-distal direction. The tabs are arranged in an arrangement around the axis of the shaft 11 and in circumferential direction around the axis spaced apart by slots 24. The slots 24 thus form a spacing in which the medical device can be admitted to project out of the receiving recess in a direction perpendicular to the axis. Although any other device fixation may be used, in this example the bore is provided with a thread extending from the opening of the bore at the top-side of the tulip towards the bottom of the bore, e.g. terminating at a distance from the bottom, to screw, as illustrated in FIG. 14, a set-screw to fixate the rod 70 or other medical device between the insert 40 and the set-crew.

As is illustrated in FIGS. 15 and 16, in the shown examples, when the head 20 is locked into position the orientation of the head 20 relative to the bone fastener 10 can still be adapted but, depending on the specific implementation, the orientation of the head may be locked as well. In an example, the orientation may be adaptable and after being adapted the head may be fixated on the head post. For instance in the example of FIG. 14, the set screw may exert via the rod a compressive force on the cage which results in fixating the head post in the cage. However, another type of fixation may likewise be applied to lock the orientation of the head after mounting.

More specifically, as explained below in more detail, when the head post side 31 and the head side 32 are coupled to each other the orientation of the head 20 can be adapted by pivoting the head 20 around a pivot point P defined by the head post side 31 and the head side 32, as is illustrated in FIG. 16. The pivot axis may have a fixed orientation or a variable orientation. In this example, the mount 30 forms a pivot joint, in particular a ball joint with the head 20 as socket and the head post 10 as ball. Additionally or alternatively, the orientation may be adapted by rotation of the head 20 around an axis extending through the head 20, without the axis changing position and over an angular range that maintains the head 32 locked onto the head post 31.

Figures 9, 10:
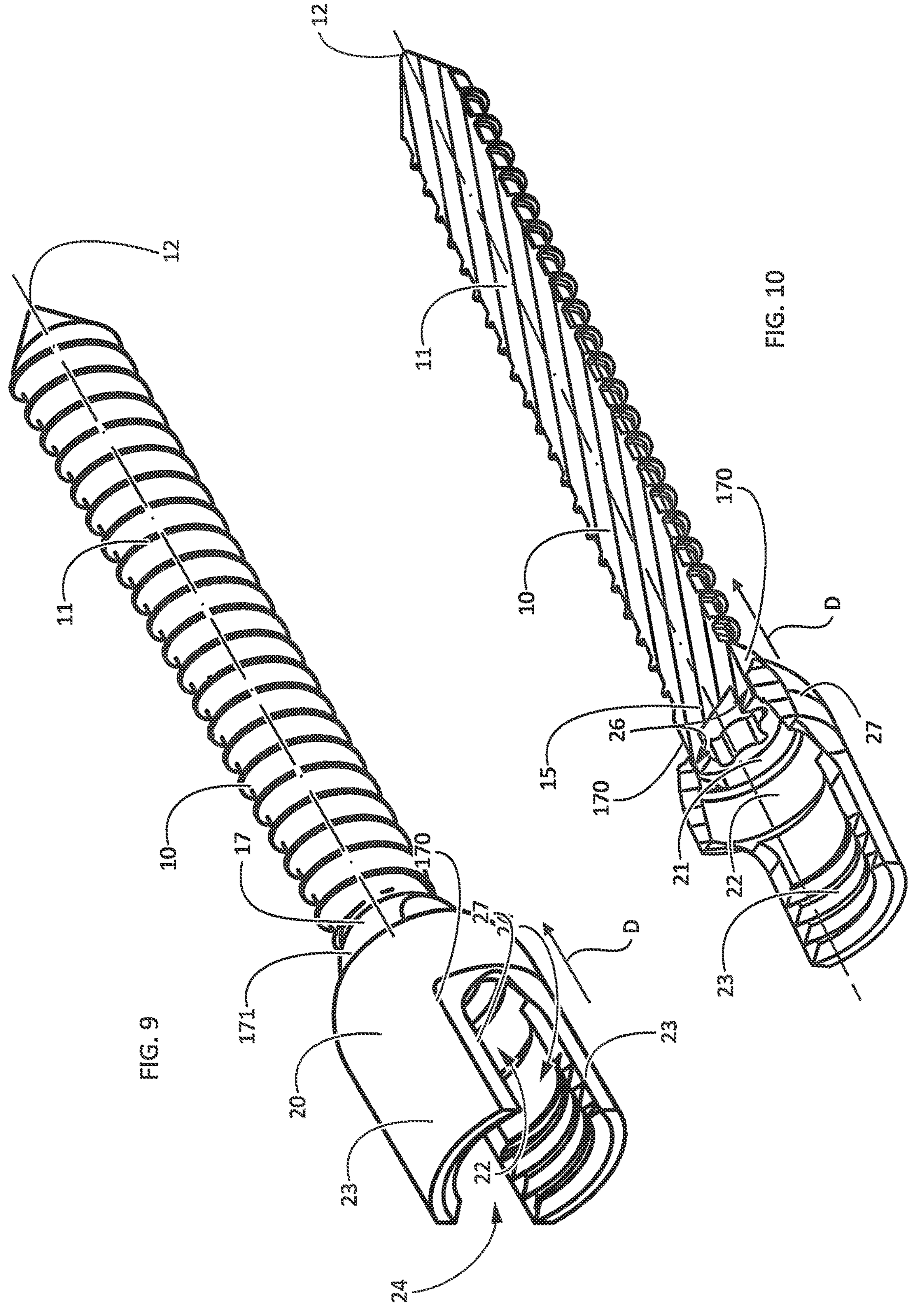
FIG. 9 schematically shows a perspective view of the example of FIG. 1 with the mount in the engaged, but not locked state illustrated in FIG. 3.
FIG. 10 schematically shows a perspective, sectional view of the example of FIG. 9.
Figure 11:
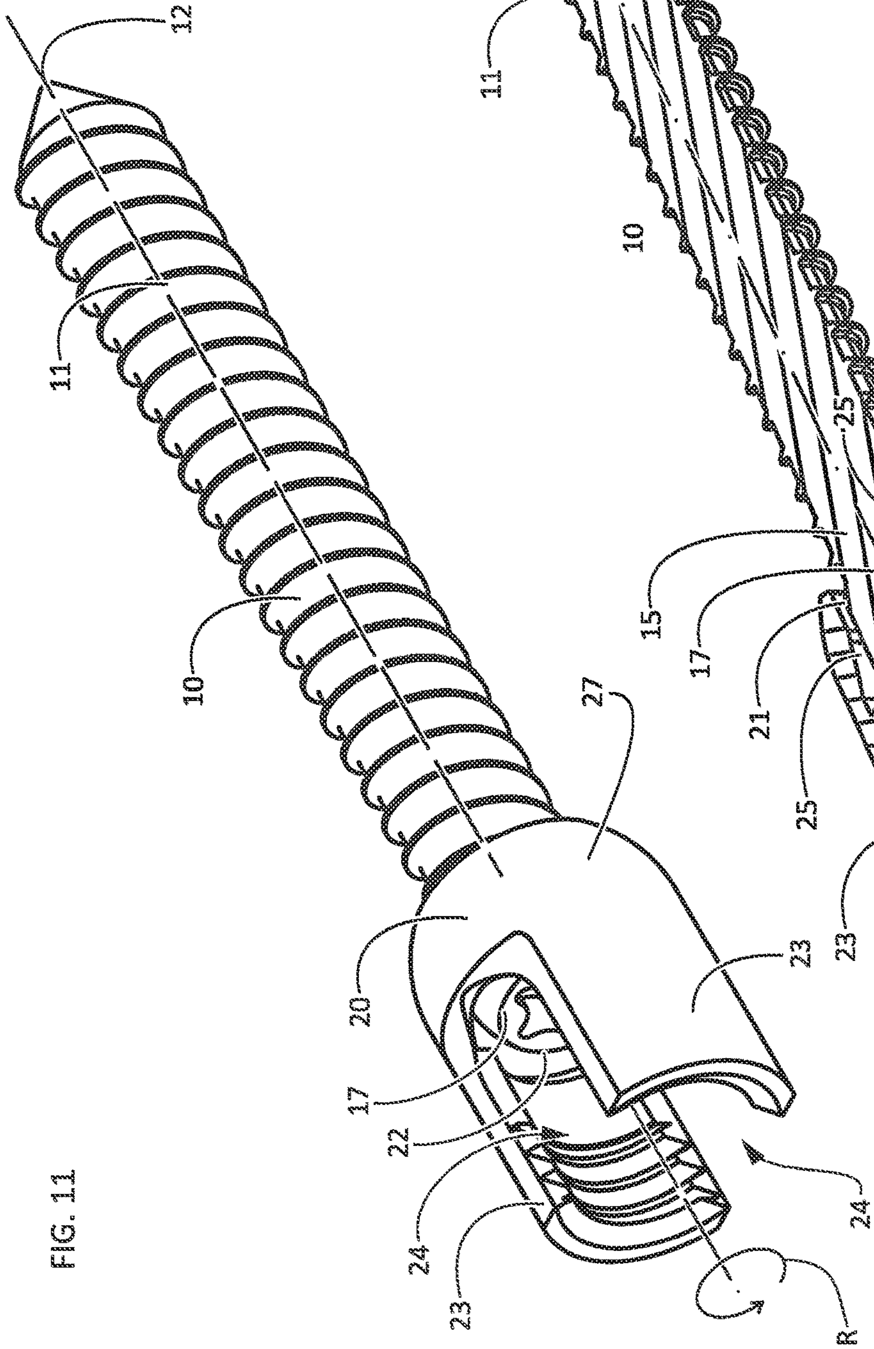
FIG. 11 schematically shows a perspective view of the example of FIG. 1 with the mount in the locked state illustrated in FIG. 6.
Figure 12:
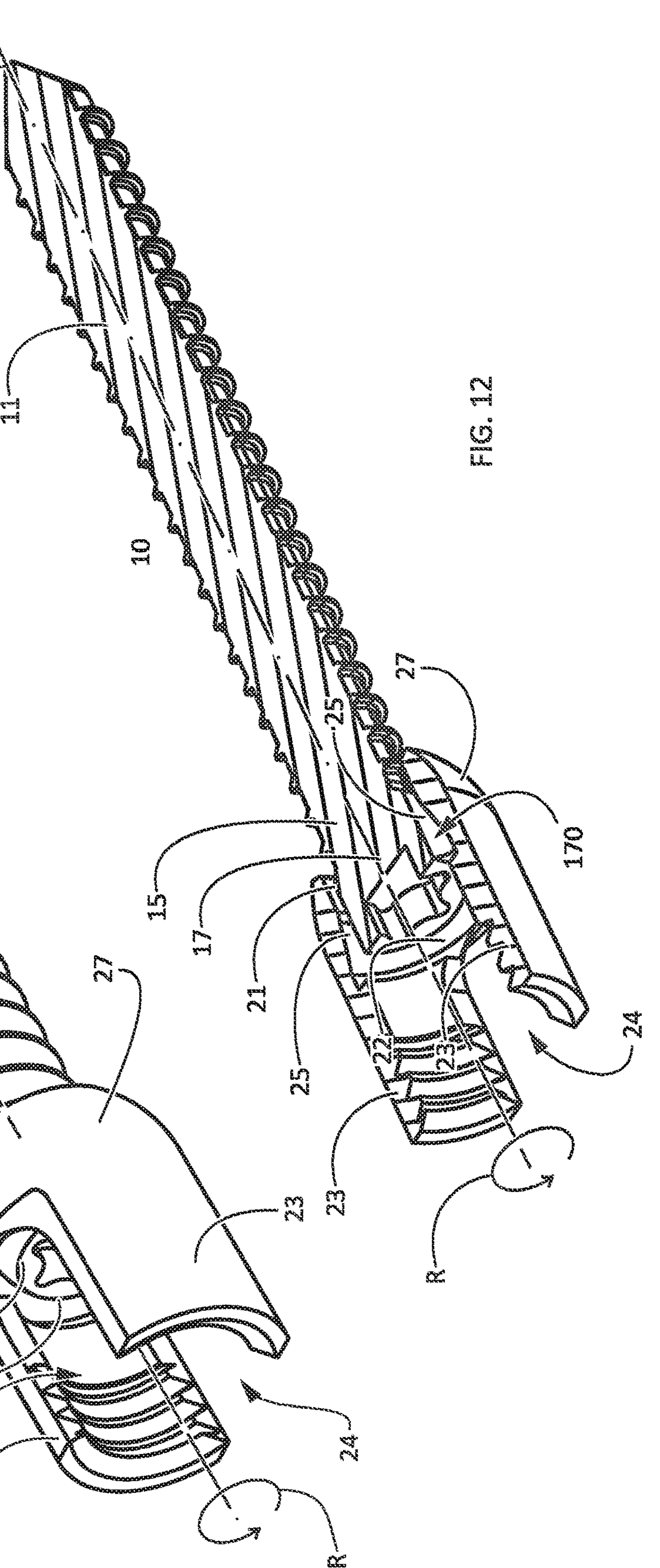
FIG. 12 schematically shows a perspective, sectional view of the example of FIG. 11.

The orthopaedic assembly may be provided in an assembled state or a non-assembled state. The orthopaedic assembly may e.g. be provided non-assembled and then be assembled during surgery, or be provided assembled and be de-assembled and reassembled to modify the orthopaedic assembly. The assembling may be performed by performing the sliding, after which the assembly may look as shown in FIGS. 9 and 10 and locking, after which the assembly may look as shown in FIGS. 11 and 12. Depending on the type of bone fastener and head post, as illustrated in FIG. 13, the pivot joint between the head 20 and bone fastener 10 may thereafter be completed by placing the insert 40. Furthermore, a mechanical, electromechanical or electronic, medical device may be attached to the head, as is illustrated in FIG. 14 for a spinal rod 70 which is fixated with the set screw as an example of the device fixation 50.

For example, the assembly may be provided in non-assembled state as a kit which comprises a set of at least two different heads. The heads can for example differ in one or more aspect, such as the angular range over which the head has to be turned to lock the head in position on the head post. For instance, the wider part of the passage may be shaped such that the round part of the head post comes to abut to the passage. Also, the head and the bone fastener may be provided separately.

The assembly, head and/or the bone fastener may be provided in a package. For example, one, more than one or all of those may be provided in a sterile package in which the mentioned objects are sealed to remain sterile. The package may comprise an enclosure and instructions for using, or an indication of usability of, the member in a method of bone surgery on a mammal, such as described below with reference to FIGS. 21-27 or other type of bone surgery.

Referring to the example of FIGS. 18 and 19, the example shown therein differs from the example described above in the following. The bone fastener 10 is provided with an expandable implant 60 to be admitted in an intra-osseous cavity. The expandable implant 60 is in this example located at the tip, more precisely between the pointed tip 14 and the thread 16. As illustrated in FIG. 19, the implant 60 is expandable in a direction of expansion perpendicular to the distal-proximal direction, and the orientation of the head 20 in which it locks into position on the head post 15, relative to the direction of expansion, is predetermined. Thus, the direction of the forces acting on the head post 15 when mounting the head 20 is predetermined, which allows to ensure that these forces do not impact the support provided by the implant 60 to the bone 100.

As explained below in more detail, the expandable implant 60 is fixated to the shaft 11. In this example the implant 60 is located adjacent to the tip 14 and at a distance from the head post 15. The implant 60 is separated from the head post 15 by the threaded part 16 of the shaft 11, which thus can serve as a bone anchor for the implant 60, to anchor the implant 60 to a part of the bone between the head post and the implant.

As an alternative to the shown implementation, instead of the expandable implant being provided as an integral part of the bone fastener (in this example at the tip), the bone fastener 10 and the expandable implant 60 may be separate, discrete devices forming part of the assembly. In such a case, the assembly may be assembled into a single device from these separate devices prior to use. For example, the bone fastener may be engageable with a separate expandable implant to assemble the assembly. For instance, the bone fastener may be provided with a coupling interface compatible with a coupling interface of the expandable implant to establish a mechanical connection or joint between the bone fastener and the expandable implant. Although a large variety of interfaces may be used, in an example the coupling interface is suitable to establish a mechanical rigid interconnection, such as a threaded joint. For instance, the tip of the shaft may be shaped as a threaded rod which can be screwed into a hole of the implant, provided with a compatible thread, for example. For instance, the example shown in FIG. 18 may be modified such that the shaft 11 is without the implant and has its tip 14 at the end of the threaded area (instead of having an not-threaded area with the expandable implant). The expandable implant 60 may be a separate device which can be screwed onto the tip 14. To assemble the orthopaedic assembly, after screwing the two devices together, the internal driving rod 18 may be placed in the hollow, axial bore in the shaft 11 to extend through a corresponding bore in the implant which terminates at the proximal side of the expandable implants.

The implant 60 has an expanded state and a non-expanded state. In this example, the expanded state is the state of maximum expansion, and the diameter of the implant in the direction of expansion can be increased over a continuous range between the diameter in the non-expanded state and the diameter in the expanded state. In alternative implementations though, for instance the implant can be expanded only step-wise, and the diameter in the direction of expansion only be set to discrete values between the diameter of the non-expanded state and diameter of the expanded state. A typical maximum expansion of the implant 60 is for example between 1.5 and 3 or 4 times the non-expanded diameter. Other maximum expansions are likewise possible, and it is currently preferred that the maximum expansion is less than 5 times the non-expanded diameter which to ensures a mechanical stable and reliable expansion.

In the shown example, the expandable implant 60 has one or more load supporting surfaces 61,62 extending parallel to the axial direction of the shaft 11, i.e. facing in a direction radially outwards. In this example, the load supporting surfaces 61,62 resist loads acting thereon in the radial direction towards the axis, which in this example is perpendicular to the load supporting surfaces 61,62. Preferably but not necessarily, the load supporting surface remains, at least in the radial direction but preferably all directions, in position relative to the shaft in response to the load acting thereon. Said differently, preferably the load supporting surface 61,62 is maintained by the implant 60 in a set position when the load acts on the surface. Although other shapes are possible, the load supporting surface 61,62 may, as in the example, be curved around an axis parallel to the axial direction, and be straight in the direction of the axis. Said differently, one or more of the load support surfaces may form a respective horizontal cylindrical segment.

The implant 60 can be transferred into the expanded state to support, when admitted in an intra-osseous cavity, the bone against a load acting thereon from outside the bone, such as a compressive load acting on an outside surface of the bone, in a direction opposite to the direction of expansion (and in this example perpendicular to the load supporting surface). Thereby, e.g. a fractured bone can be stabilized. For instance, the expandable implant 60 may be a vertebral augmentation device for reinforcing the internal structure of a vertebra by resisting from inside the vertebra compressive loads acting from the outside on the vertebral endplates of the vertebra. In this respect, the expandable implant may during transfer from the non-expanded state to the expanded state, be in or come into contact with the bone. Said differently, one or more of the load supporting surfaces of the expandable implant 60 may upon starting, or during expansion, contact the bone inside the bone, and upon further expansion push against the bone in a direction towards the outside of the bone. This pushing may deform the bone from the inside such that the outside surface of the bone is pushed outwards in the direction of expansion. This allows to restore the outside shape of a damaged bone, e.g. a collapsed bone. For instance, the expandable implant 60 may be a vertebral augmentation device which can be oriented with the load support surface(s) facing one or more of the vertebral endplates and which in case of a collapsed vertebra can be expanded to partially or completely restore the height of the collapsed vertebra.

The implant 60 may comprise one, two or more movable pieces, such as a plate or a bulk block, each with a respective load supporting surface 61,62 for supporting a wall of the intra-osseous cavity against a load acting on the bone. The movable pieces are movable away from the shaft 11 in a direction of expansion. In this example, they are translationally movable, without rotational movement. However, they may be implemented to make a combined translational-rotational movement. In a preferred example, the movement is rectilinear but this may be curvilinear as well. The direction of expansion is in this example perpendicular to the longitudinal direction l of the shaft 11. The displacement of the movable piece brings the load supporting surface 62,62 from an initial position, that is in the non-expanded state, shown in FIG. 18 to an expanded position in the expanded state, shown in FIG. 19. When correctly positioned in the cavity, the load supporting surface 60,61 then abuts to the wall of an intra-osseous cavity 105 and supports the bone matter from which the wall is made, e.g. against a load acting thereon from outside the bone, such as a compressive load acting on an outside surface of the bone in a direction opposite to the direction of expansion.

To drive the expansion of the expandable implant 60, the bone fastener 10 may be provided with a drive part 18. As can be seen from FIG. 19, as an example of a drive part 18 an internal driving rod extends axially through a hollow bore in the shaft 11, which is accessible at the distal end 13 for an expansion tool. By rotation of the driving rod the implant can be expanded, as is described in applicant's Dutch application NL 2026145, the contents of which are incorporated herein by reference.

The orthopaedic assembly 1 may be provided in a non-assembled state. A method of assembling the orthopaedic assembly may be applied thereto to bring the orthopaedic assembly in the assembled state. Such a method may e.g. be performed during surgery as part of an invasive procedure. For example, the head 20 may be mounted after the bone fastener 10 has been inserted into the bone, without the head thereon, e.g. into a part of a vertebra such as the pedicle. The surgeon or other medical practitioner may then e.g. select a head, mount the head onto the bone fastener fixated in the bone and then e.g. mount a medical device onto the head, such as a rod to stabilize (parts of) the bone. There may be a time interval between placing the bone fastener 10 and mounting the head 20. The head 20 may for example be mounted post-surgery when the bone fastener 10 has osseo-integrated into the bone sufficiently, and optionally the wound has been healed, with the head post 15 projecting out of the body of the subject, for example.

Alternatively, the method of assembling can be a non-invasive, non-surgical method, completely performed outside the mammalian body and without physical intervention thereto. In such a case, the method can be performed prior to surgery, for example. For instance, the method may be performed in a manufacturing facility and generally at any point in time prior to the bone fastener being used in the actual surgery, and even in-situ in the operating facility. For example, the assembly 1 may be packaged in a non-assembled state and be taken out of the package in the operating facility to be put in the assembled state. For example, a medical practitioner may select out of a set of heads the one deemed most suitable for the specific subject, e.g. based on the position and the orientation of the screw, the structure of the bone, the type of surgical procedure etc. . . . . The head 20 may then be mounted on the bone fastener 10 to assemble the assembly 1, which can thereafter be used in the orthopaedic procedure.

In the method of assembling, the first lockable part 31 may be slid over the second lockable part 32 to admit the second lockable part in the opening, as is indicated with the arrows D in FIGS. 9 and 10, for example. Thereafter, when the second lockable part is admitted to a predetermined depth into the opening, the head 20 may be locked on the head post 15. To that end, the head is turned around an axis parallel to the distal-proximal direction, as indicated with the arrow R in FIGS. 11 and 12.

In the shown examples, the mount 30 is non-destructively releasable. After assembling, the orthopaedic assembly 1 may be easily disassembled by releasing mount. To that end, the head 20 can be rotated in the direction opposite to the direction of turning, thereby unlocking the head, and then retracting the second lockable part from the opening to separate the head 20 from the bone fastener 10. For example, in case a medical practitioner decides, during or prior to the operation, that another head is more suitable than the one pre-assembled, a pre-assembled orthopaedic assembly 1 may be disassembled to replace the head 20. Also, post-surgery, when the bone to be treated has healed and accordingly the orthopaedic assembly, or at least the head thereof, is not needed anymore, the head may be removed without requiring surgery. For example, the head may be removed to provide the medical practitioner access to the bone fastener and allow the bone fastener to be unscrewed, out of the bone, to complete the treatment, or alternatively the bone fastener 10 may be left in the bone 100. Alternatively, upon locking the mount 30 may establish a permanent attachment of the head 20 on the head post 15 which is only destructively releasable.

Figure 20:
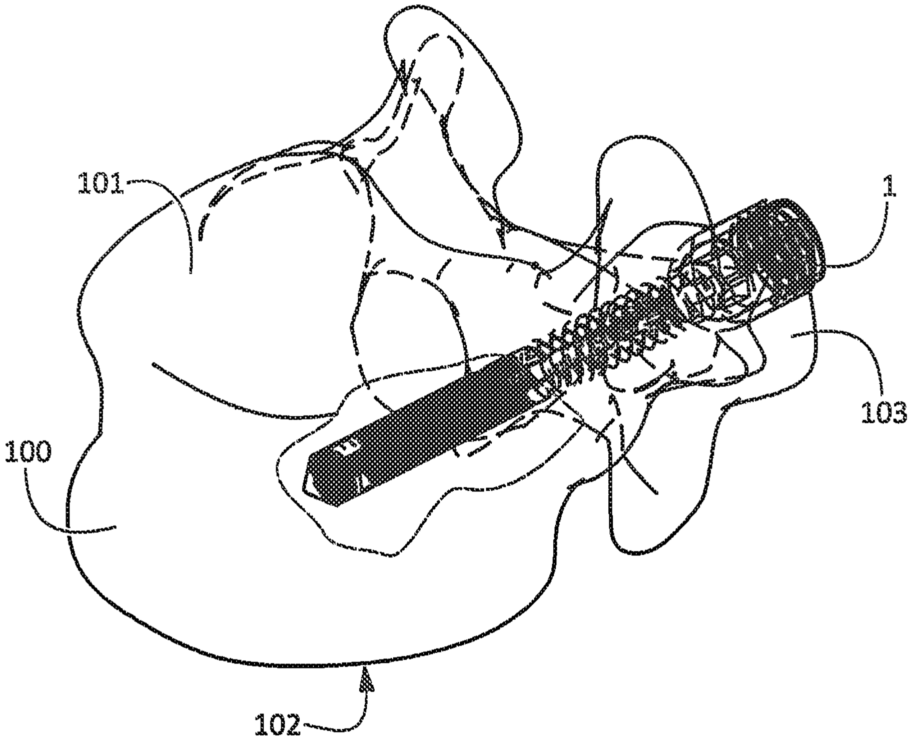
FIG. 20 shows a perspective view of an example of a bone with the example of FIG. 17 placed thereinto.

Referring to FIGS. 20-27, the application of examples of assemblies is illustrated, in these examples in a method of surgery of a living, human or non-human, mammalian body. As an example of a bone 100, the assembly 1 is shown in FIG. 20 anchored in a human vertebra, which as shown has a vertebral body with endplates 101,102 and a vertebral pedicle 103. In such a method an incision may be made in the mammalian body; and the assembly 1 is inserted in a bone. As illustrated in FIG. 21, for example a cannula 104 may be pre-prepared in the vertebra, e.g. through the pedicle in case of a pedicle screw.

As illustrated in FIG. 22, the bone fastener 10 can for example be anchored in the pedicle, without the head 20 mounted on the head post 15, by rotating the bone fastener 10 and thereby screwing the shaft 11 in the cannula 104, until the tip 14 is at the desired depth. For example, the assembly 1 may be inserted in a pre-made cannula 104 in the bone 10 with the tip 14 first, until the thread 16 enters the cannula. Up to this point, the bone fastener may e.g. be slid, without rotation into the cannular 104. In the shown examples, the thread 16 extends from the tip 14 up to the head post 15, but alternatively between the tip 14 and the thread 16 the shaft may have an unthreaded, for example smooth, part which can be slid into the cannular 104. Upon further insertion, the shaft 11 starts frictionally anchoring in the cannula. In this example by rotating the assembly 1 the shaft 1 will tread the wall of the cannula 104, and this thread-forming insertion can then be continued. During this, in the shown example, the assembly 1 remains in the non-assembled state.

Figure 23:
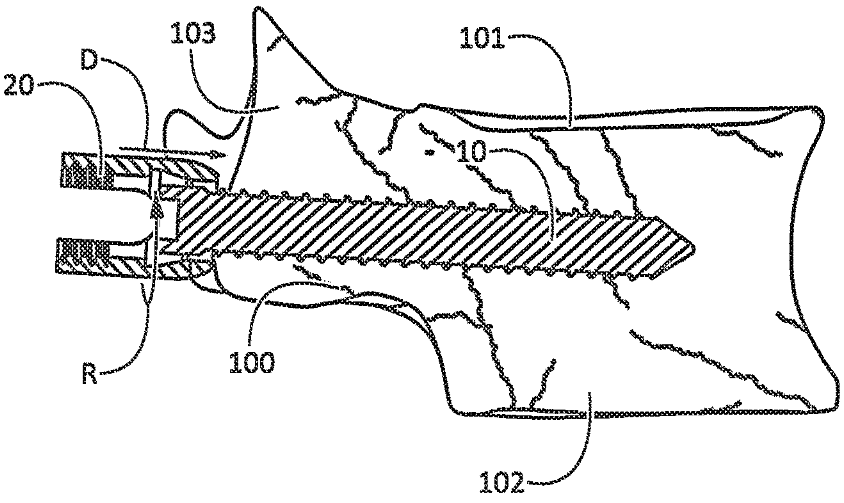

When the proximal end 12 is at the desired depth in the cannula 104 (or said differently the distal end 13 is at the desired distance from the outer surface of the bone, and e.g. projects a desired distance out of the bone, is flush with the outer surface or recessed to a desired depth in the bone), the assembly 1 may be assembled, as is illustrated in FIG. 23 with the arrows D and R. FIG. 23 shows the assembly 1 in the assembled state.

Figure 24:
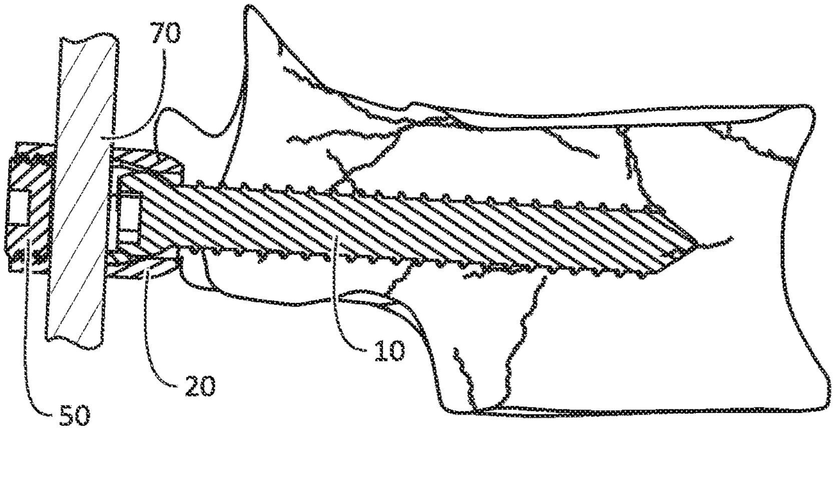

Thereafter, the assembly 1 may be completed e.g. by finalising the pivot joint between the head and the head post and/or mounting a medical device. To finalise the joint, for example, the insert 40 may be placed in the void 22, with the spherical side 42 of the split ring facing the bulge 17, to complete the socket of the ball-joint. To mount a medical device, a part thereof—such as the rod 2—can be clamped in the void 24, by means of the device fixation 50. FIG. 24 shows the completed assembly with as a medical device a spinal rod 2 clamped by the device fixation 50. The rod 2 extends from a respective slot 24 through the void 22 to another slot 24. The rod 2 projects out of the void in a direction non-parallel to the distal-proximal direction with a respective end of the spinal rod 2 from one or more of the slots 24 such that the spinal rod 2 can be attached to another, similar or different, orthopaedic assembly placed in another vertebra for example.

Figure 25:
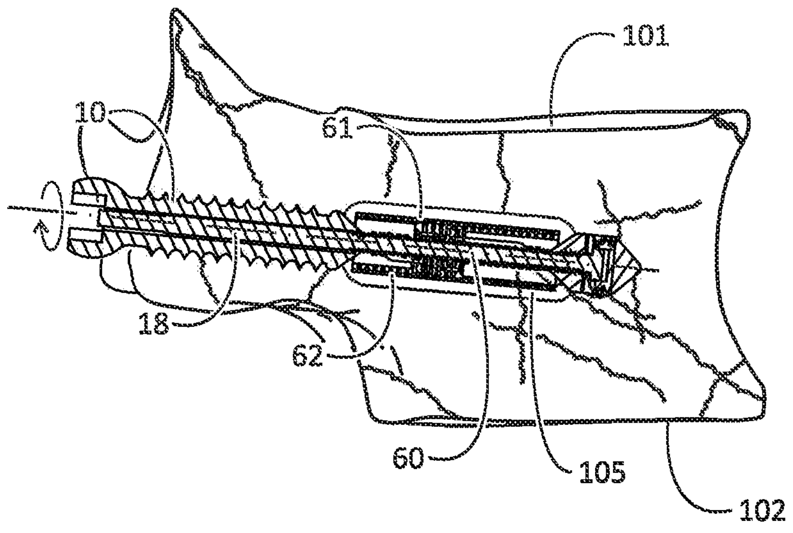
FIG. 25-27 show side views of a bone, during successive stages of an example of a procedure of fixating the example of FIGS. 18 and 19 into the bone.
Figure 26:
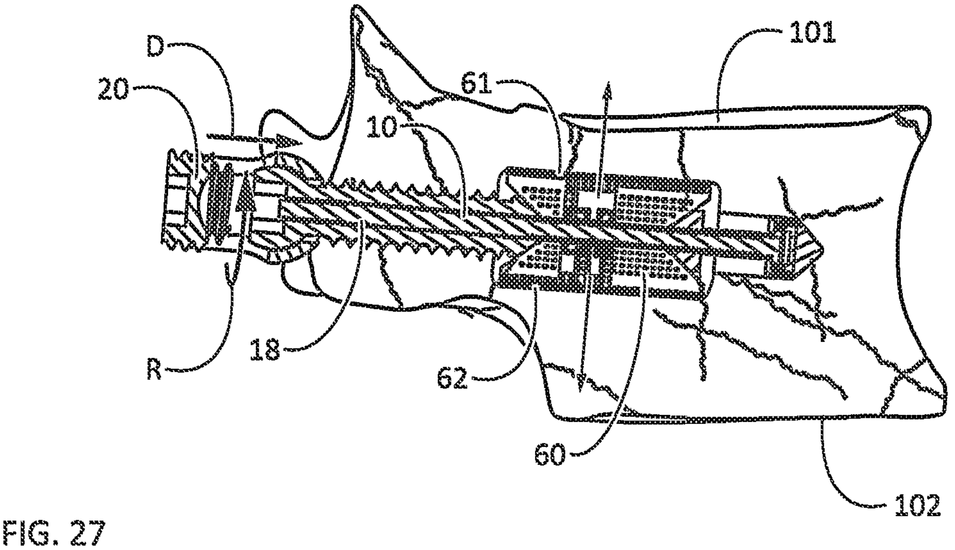
Figure 27:
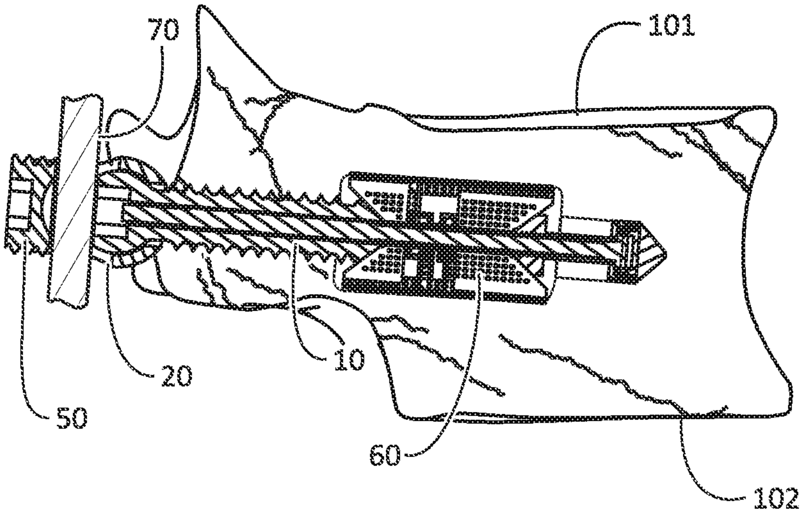

Referring to FIGS. 25-27, the example shown therein uses a bone fastener 10 provided with an expandable implant 60. The method is largely the same as of the example of FIGS. 21-24, but differs in the following.

When inserting the bone fastener 10 into the cannula 104, not only is the tip 14 brought into the bone to the desired depth, but the load supporting surfaces 61,62 are oriented as the medical practitioner deems appropriate for the direction in which the implant 60 is to be expanded and the location at which the implant 60 is to provide support to the bone 100. The bone fastener 10 makes positioning the implant 60 less cumbersome because the orientation of the implant, which is not visible, can be deduced from the orientation of the head post 15. In this example, the head 20 is not yet mounted and the bulge 17 will be exposed and available for visual inspection and the orientation of the non-spherical shape of the bulge 17 can be perceived by the medical practitioner without use of tools like an X-ray imaging device. The orientation of the implant is dependent on the orientation of the non-spherical shape of the bulge 17 because these are at a predetermined, fixed, angle relative to each other, seen in the axial direction of the shaft 11.

Illustrated in FIG. 25-27 is a cavity 105 in the vertebral body, e.g. a not naturally occurring one such as made by the surgeon or other medical practitioner during the surgical procedure. In this example, the intra-osseous cavity 105 has been pre-prepared to be located close to the surface of the bone on which the external load acts, in this example the upper vertebral endplate 101. The bone fastener 10 is placed into a depth where the implant 60 is in the cavity 105. For example, 5 mm or less, such as 4 mm or less, such as 3 mm or less of bone tissue may be present between the upper load supporting surface 61 of the implant 60 and the endplate 100. This allows an elastic or plastic deformation of this tissue by the load supporting surface 61 pushing against the vertebral endplate 101 upon expansion and accordingly allows to reduce the risk of bone fracture or collapse when expanding the implant 60 (e.g. to partially or completely restore the vertebral height). For instance, 1 mm or more, such as 2 mm or more, for example 3 mm of tissue may be present between the upper load supporting surface 61 and the vertebral endplate. This reduces the risk that the implant 60 pierces through the tissue and becomes exposed during expansion or post-surgery.

Additionally, as illustrated, the tip 14 can be positioned close to the anterior wall of the vertebra. For instance, the bone fastener 10 may be positioned such that there is 1 mm or more, such as 2 mm or more, such as 3 mm or more of space, e.g. with spongy bone material, left between the tip 14 and the anterior wall. Preferably, this space is 8 mm or less, such as 6 mm or less, for example 5 mm or less. This allows to avoid piercing of the anterior wall by the bone fastener 10. The position of the bone fastener 10 may be determined prior to expansion, for instance, via imaging techniques well known in the art, so as to ensure the implant is fully inside the vertebral body, and e.g. is not in the pedicle.

When the assembly 1 is at the desired depth and the load supporting surfaces 61,62 are oriented in the desired direction, the implant 60 is driven to expansion. The anchoring of the bone fastener 10 in the bone 100 and the expansion of the expandable implant 60 may be performed as separate steps with the expansion after the anchoring, such as directly succeeding each other. This allows to increase the control over the torque required to anchor the bone fastener 10 and/or the pressure exerted at the interface between the load supporting surface 61 and the bone 100 during expansion. Upon expansion of the implant 60, the load supporting surface 61,62 move outwards in a direction of expansion d, which in this example is perpendicular to the distal-proximal direction and parallel to the sagittal plane. FIG. 26 shows the bone fastener 10 with the implant 60 in the expanded state. The expansion may e.g. be driven form the distal end of the bone fastener 10, in the shown example via the drive part 18. FIG. 26 shows the implant 60 completely expanded, but the implant 60 may be expanded to less than the maximum expansion.

In this example, after expansion of the implant 60, the head 20 is mounted on the bone fastener 10 and the assembly 1 is assembled. FIG. 27 shows the assembly 1 in the assembled state with the head 20 locked on the head post 15. The mount allows to mount the head 20 without perturbating the position of the implant 60. Like the example of FIGS. 21-24, the assembly is completed by finalising the pivot joint between the head 20 and the bone fastener 10 and mounting a medical device on the head 20. For example, a rod 70 may be used to couple the bone to other bones such that compressive forces acting on the bone in the direction of expansion are reduced. In case the assembly 1 is a poly axial or uniplanar assembly, the orientation of the head 20 may then be adapted to align the direction of thereof as deemed suitable for connecting a medical device, e.g. rod 70. After adapting the orientation, the head 20 may then be fixated. In this example, the joint may be locked by tightening the set screw to the extent that the compressive force acting on the pivot joint locks the joint. More specifically, on the insert 40 a compressive force is exerted by the set screw via the rod that clamps the head post in the cage.

In the foregoing specification, the invention has been described with reference to specific examples of embodiments of the invention. It will, however, be evident that various modifications and changes may be made therein and that the examples are not intended to limit the scope of the claims.

For example, although in the example a bone fastener for spinal surgery has been described, the bone fastener 10 can be implemented to be used in other bones. Furthermore, the head 20 may provide an anchor for other medical devices than a rod. For instance, this can be implemented as an anchor for transfixation pins to which a connecting bar may be fixated in external or internal skeletal fixation. The head can alternatively or additionally be implemented as stem for, for example, an artificial femoral, hip or shoulder joint. Likewise, the head can be implemented as an anchor for an electronic medical device or for a medical device releasing a pharmaceutically active component.

Furthermore, the orthopaedic assembly 1 may be used in a bone fixation system. Such as system may comprises at least two orthopaedic assemblies, and one or more connector rods attachable to the heads for fixating the bone fasteners relative to each other, e.g. such as for a spinal fixation system.

Also, the parts of the orthopaedic assembly may be made of any suitable biocompatible material. The material may for example contain a material out of the group consisting of: metals, metal compounds, metal alloys, metal composites, polymers, ceramics and combinations of materials of this group. The biocompatible material can contain a metal out of the group consisting of: titanium, tantalum, niobium, stainless steel, cobalt chrome alloys, zirconia, or a compound, alloy or composite thereof. Other suitable biocompatible materials can contain a polymer out of the group consisting of polyaryletherketone, polyether ether ketone, polyetherketoneketone. In this respect, all parts of the bone fastener may be made of the same material or different parts may be made of different materials.

One, or more than one, or all of the parts may be non-degradable in-vivo or in-situ. This allows a permanent structure. For example, the anchoring part may be made of a non-degradable metal containing material, whereas e.g. a movable piece made be made of a degradable material. Alternatively, or additionally, one, or more than one, or all of the parts may be bio-degradable in-vivo. This allows e.g. to place a temporary bone fastener, or a bone fastener with temporary parts, without requiring surgery to remove the bone fastener. Also, for instance, the bio-degradable degradable part may fill a gap between a non-degradable part and tissue to be regrown, such as bone. This allows e.g. placing a bone fastener at a location in a space larger than the bone fastener, expanding the bone fastener such that the degradable part bridges the space between the non-degradable part and the edge of the gap. The degradable part can then disappear while the gap fills, e.g. by tissue regrowth.

The shaft 11 may for example be made from materials different from the movable pieces of the expandable implant 60. This allows them to have different properties, such as a rigid shaft 11 and a flexible movable piece or vice-versa. One, or more than one, or all of the shaft 11 and movable pieces may be non-degradable in-vivo or in-situ. This allows a permanent bone fastener, e.g. suitable for a bone fastener which serves as an anchor for a prosthesis.

Alternatively, or additionally, one, more than one, or all of the shaft 11 and movable pieces 4 may be bio-degradable in-vivo. This allows e.g. to place a temporary bone fastener without requiring surgery to remove the bone fastener 10, or a bone fastener with temporary parts. For example, the bone fastener 10 may be biodegradable while the head 20, or at least a core thereof, is made of a non-degradable material, such as a non-corrosive, non-toxic metal or alloy. This allows to anchor the bone fastener 10 during the healing period with the head 20 mounted thereon and remove the bone fastener with, minimal or non, invasive procedure. The head 20 can for instance, after a healing period be demounted from the head post 15 prior to biodegrading of the bone fastener, by unlocking and sliding the head in the direction opposite to the mounting direction. Thereafter, the bone fastener 10 may be left in the bone to biodegrade. In addition, for example an outer sleeve of the shaft 11 with the thread 16 may be biodegradable while a rod-shaped core surrounded by the sleeve is made of a stiff, non-degradable material (e.g. Ti or biocompatible Ti-alloys). This similarly allows to firmly anchor the bone fastener 1 during healing while, due to the degrading of the outer sleeve, after healing the shaft 11 be easily removed. In such a case, for example, in case the bone fastener is provided with the expandable implant, the expandable part can be left in the bone, e.g. when it has completely osseo-integrated therein.

In this, for instance, the non-degradable parts to be removed after healing, may have a closed-surface to avoid integration in the bone tissue, such as to avoid osseo-integration in the bone. The degradable parts may have an open, porous surface to allow integration. Alternatively, the non-degradable parts may integrate into the bone 100. For example, the shaft 11 may be biodegradable. This allows to initially anchor the bone fastener 1. When the shaft 11 degrades and the implant 60 integrates, e.g. by osseo-integration, the adherence between the integrated parts and the bone can take over the anchoring function. This allows e.g. to reduce prolonged locally high pressure caused by the bone fastener 10 pressing into the bone 100 and, without being bound to theory, is believed to reduce secondary complications post-surgery.

Furthermore, one, more than one or all of the bone fastener 10, the head 20, the load supporting parts of the expandable implant 60 or other elements may be a monolithic body, e.g. formed during manufacturing as a single piece or composed of separately manufactured parts welded or otherwise joined together to form the monolithic body.

Figure 28:
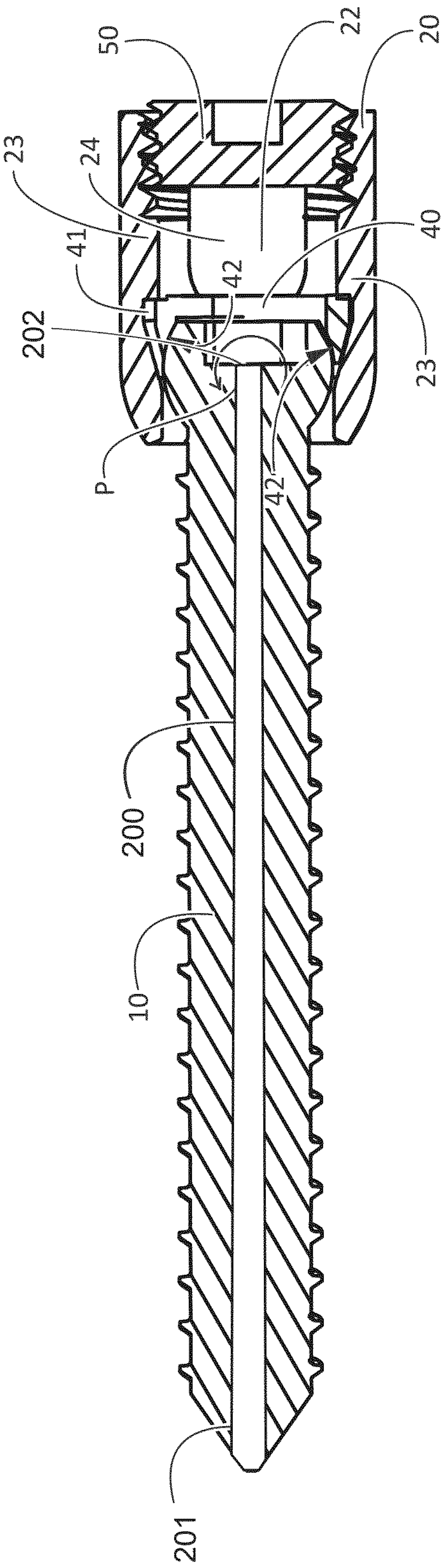
FIG. 28 schematically shows a sectionable side view of FIG. 15 with a cannulated shaft.

In the shown examples, the inside of the shaft 11 is massive, however the shaft 11 may have hollow parts. For example, the bone fastener may comprise or be connectable to an injector for injecting a fluid, for example a liquid such as bone cement into the bone. In such a case, for instance, the shaft may be cannulated, with one or more channels 200 extending through the inside the shaft, as illustrated in FIG. 28. Each channel may have an inlet port 202 connectable to a supply of liquid, such as bone cement, or other fluid and one or more outlet ports for injecting the liquid, such as bone cement, or other fluid into the bone. For example, the inlet port 202 may be located at the distal end 13, at a position which remains exposed and connectable to the supply when the bone fastener 10 is mounted, and one or more, or all, of the outlet ports 201 may be located at a position away from the distal end when the bone fastener 10 is mounted is inside the bone. For instance, the location of an outlet port may be at the tip, or at the side of the shaft between the tip and the distal end, for instance in the threaded part or in an non-threaded area (such as the length between the thread 16 and the proximal end 12 in the example of FIGS. 18 and 19). For example, in case of a pedicle screw the location of the outlet may be in the area between the distal end and a position at a distance therefrom corresponding to the depth of the pedicle, which allows to inject bone cement to fixate the fastener to the pedicle. Alternatively or additionally, one or more outlets may be located in the area between that position and the tip, which allows to inject liquid, such as bone cement, or other fluid into the vertebral body. This may e.g. fill fractures therein and/or, in case of an expandable implant such as described being used, fixate the expandable implant to the walls of the intra-osseous cavity. In a currently preferred example, a straight channel or cannula extends from the distal end up to the tip, through the axis of the shaft 11. The channel may have an inlet 200 at the head post 15 and mouth at an outlet at the tip and. In a simple embodiment the channel is unbranched, but e.g. branch channels may be present which connect the channel to outlets located at the longitudinal sides of the shaft 11.

Likewise, where a movement of an object is described (e.g. in relation to another object) it will be apparent that, unless explicitly specified otherwise, this is a relative movement, and accordingly depending on the chosen reference frame, the object may be moving relative to an observer while the other object is static, the other object may be moving while the object is static relative to the observer or both objects may be moving, but differently, relative to the observer. Moreover, the terms “front,” “back,” “top,” “bottom,” “over,” “under” and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word “comprising” does not exclude the presence of other elements or steps then those listed in a claim. Furthermore, the terms “a” or “an,” are used herein in the sense of “one or more than one” and do not exclude multiple of the specified elements being present. Also, the use of introductory phrases such as “at least one” and “one or more” in the claims should not be construed to imply that the introduction of another claim element by the indefinite articles “a” or “an” limits any particular claim containing such introduced claim element to inventions containing only one such element, even when the same claim includes the introductory phrases “at least one” or “one or more” and indefinite articles such as “a” or “an.” The same holds true for the use of definite articles. Unless stated otherwise, terms such as “first” and “second” are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

LIST OF REFERENCE NUMBERS

1 orthopaedic assembly
2 rod
3 tool
10 bone fastener
11 shaft
12 proximal end
13 distal end
14 tip
15 head post
16 thread
17 bulge
18 drive part
19 spherical section
20 head
21 opening
22 void
23 tab
24 slot
25 annular gap
26 flattened side
27 head body
30 mount
31 head post side
32 head side
33 first lockable part
34 second lockable part
35 insert
41 gap
42 spherical annular side
50 device fixation
60 expandable implant
61 upper load supporting surface

62 lower load supporting surface
63 driving rod
70 spinal rod
100 bone
101 vertebral endplate
102 vertebral endplate
103 vertebral pedicle
104 cannula
105 cavity
170 flattened side
171 spherical segment

The invention claimed is:

1. An orthopaedic assembly, comprising:

a bone fastener comprising:

- a shaft for fastening the assembly to a bone, the shaft having a proximal end and a distal end, the proximal end forming a tip of the bone fastener, and
- a head post located at the distal end, for mounting a separate head on the bone fastener;

the assembly further comprising:

the head;

a mount for mounting the head on the head post, the mount comprising an opening in a first lockable part in which a second lockable part of the mount can be admitted, wherein the head and the head post are each provided with a respective one of the first lockable part and the second lockable part;

wherein the head is mountable on the head post by:

- first moving the head towards the head post and thereby sliding the first lockable part over the second lockable part in a sliding direction to admit the second lockable part in the opening, and
- locking the head on the head post, once the second lockable part is admitted to a predetermined depth into the opening, by turning the first lockable part relative to the second lockable part around an axis extending in the sliding direction;
- wherein the bone fastener is a poly-axial screw and after locking the head onto the head post, the head retains an axial freedom of motion around multiple, different axes perpendicular to the axis extending in the sliding direction;
- wherein at least after said locking:
- the first lockable part and the second lockable part form a ball-socket joint,
- the opening defines a socket of the ball-socket joint,
- the second lockable part comprises a ball of the ball-socket joint, and
- the opening mouths into a cage which defines a pivot point of the ball-socket joint, the cage having a running surface over which a contact surface of the ball of the ball-socket joint is rotationally movable around a pivot axis through the pivot point; and
- the assembly comprises a device fixation arranged to exert a blocking force on the ball-socket joint which blocks rotational movement of the ball in the socket, for blocking after locking the head onto the post the axial freedom of motion and fixating the angle between the bone fastener and the head.

2. The orthopaedic assembly of claim 1, comprising an expandable implant located at or connectable to the tip of the bone fastener, which is expandable to support the bone against a load acting thereon from outside the bone.

3. The orthopaedic assembly of claim 2, wherein the expandable implant is expandable in a direction of expansion perpendicular to a longitudinal direction of the shaft, for supporting the bone against a load acting thereon from outside the bone in a direction opposite to the direction of expansion.

4. The orthopaedic assembly of claim 2, wherein the expandable implant comprises at least one movable piece with a respective load supporting surface, for supporting a wall of an intra-osseous cavity of the bone against the load, which movable piece is movable away from the shaft in a direction of expansion of the expandable implant to bring the load supporting surface from an initial position, in a non-expanded state of the expandable implant, to an expanded position further away from the shaft than the initial position, in an expanded state of the expandable implant.

5. The orthopaedic assembly of claim 2, wherein the expandable implant is a vertebral augmentation device for reinforcing the internal structure of a vertebra by resisting from inside the vertebra compressive loads acting on the vertebral endplates of the vertebra.

6. The orthopaedic assembly of claim 1, wherein the shaft is cannulated for injecting a fluid into the bone.

7. The orthopaedic assembly of claim 6, wherein the shaft comprises at least one channel extending through the inside of the shaft, the channel comprising an inlet port connectable to a supply of bone cement or other fluid and at least one outlet port for injecting the fluid into the bone.

8. The orthopaedic assembly of claim 1, wherein the head is mountable by moving the head in a distal-proximal direction from the distal end towards the proximal end, and the head lockable in position by turning the first lockable part around an axis parallel to the distal-proximal direction.

9. The orthopaedic assembly of claim 1, wherein:

- the second lockable part comprises a ball shaped bulge, which fits into the opening when in a fitting orientation;
- the opening mouths into a void, the void having a shape which differs from that of the opening, in which void the bulge fits both in an initial orientation corresponding to the orientation when exiting the opening and entering the void, as well as in a locked orientation where the bulge is rotated over an angle relative to the initial orientation around an axis parallel to the sliding direction; and
- the bulge does not fit into the opening when in the locked orientation.

10. The orthopaedic assembly of claim 9, wherein the void is open at an open side opposite to the opening and the orthopaedic assembly comprises a blocking element fixatable in the first lockable part to block the open side and inhibit the bulge from exiting the void at the open side.

11. The orthopaedic assembly of claim 9, wherein the second lockable part is rotatable over a predetermined range in which the bulge has a non-fitting position where at least a part of a projection of the bulge onto the opening is not overlapped by a cross-sectional shape of the opening, the range comprising a subrange where the second lockable part is in a completely locked orientation where the parts of the projection not overlapping with the cross-sectional shape are at a maximum.

12. The orthopaedic assembly of claim 1, wherein the bone fastener is a pedicle screw.

13. The orthopaedic assembly of claim 1, wherein the second lockable part has a ball shape with at least one flattened side extending parallel to the distal-proximal direction, and the opening has a round, non-circular cross-section perpendicular to the distal-proximal direction and flattened side parallel to the distal-proximal direction.

14. The orthopaedic assembly of claim 1, wherein the head post is shaped to engage with a tool to exert a torque on the bone fastener and the head post comprises an interface for engaging the tool, the interface being accessible with the tool after the first lockable part has been slid over the second lockable part and, optionally, after the head has been locked on the head post.

15. The orthopaedic assembly of claim 1, wherein, when the head is mounted on the mount, the second lockable part projects out of the opening and an annular gap is present between the second lockable part and the first lockable part in a side of the second lockable part facing away from the opening and further comprising an insert mountable inside the first lockable part to fill the annular gap.

16. The orthopaedic assembly of claim 1, wherein the head has a U-shaped cross section.

17. The orthopaedic assembly of claim 1, wherein the device fixation is configured to fixate a medical device onto the head.

18. The orthopaedic assembly of claim 17, wherein the head is a tulip head.

19. A method of assembling an orthopaedic assembly, the orthopaedic assembly comprising:

a bone fastener comprising:

a shaft for fastening the assembly to a bone, the shaft having a proximal end and a distal end, the proximal end forming a tip of the bone fastener, and a head post located at the distal end, for mounting a separate head on the bone fastener;

the assembly further comprising:

the head;

a mount for mounting the head on the head post, the mount comprising an opening in a first lockable part in which a second lockable part of the mount can be admitted, wherein the head and the head post are each provided with a respective one of the first lockable part and the second lockable part;

wherein the head is mountable on the head post by:

first moving the head towards the head post and thereby sliding the first lockable part over the second lockable part in a sliding direction to admit the second lockable part in the opening, and locking the head on the head post, once the second lockable part is admitted to a predetermined depth into the opening, by turning the first lockable part relative to the second lockable part around an axis extending in the sliding direction;

the method comprising:

sliding the first lockable part over the second lockable part in the sliding direction to admit the second lockable part in the opening; and thereafter, when the second lockable part is admitted to a predetermined depth into the opening, locking the head on the head post by turning the head around an axis extending in the sliding direction;

wherein the bone fastener is a poly-axial screw and after locking the head onto the head post, the head retains an axial freedom of motion around multiple, different axes perpendicular to the axis extending in the sliding direction;

wherein at least after said locking:

the first lockable part and the second lockable part form a ball-socket joint, where the opening defines a socket of the ball-socket joint, the second lockable part comprises a ball of the ball-socket joint, and the opening mouths into a cage which defines a pivot point of the ball-socket joint, the cage having a running surface over which a contact surface of the ball of the ball-socket joint is rotationally movable around a pivot axis through the pivot point; and and the method further comprises, after said locking, blocking the axial freedom of motion and fixating the angle between the bone fastener and head after locking the head onto the post, said blocking comprising applying by a fixation a blocking force on the ball-socket joint which blocks rotational movement of the ball in the socket.

* * * * *